United States Patent
Heilmann et al.

(10) Patent No.: US 10,258,038 B2
(45) Date of Patent: *Apr. 16, 2019

(54) USE OF HETEROCYCLIC COMPOUNDS FOR CONTROLLING NEMATODES

(71) Applicant: BAYER CROPSCIENCE AKTIENGESELLSCHAFT, Duesseldorf (DE)

(72) Inventors: Eike Kevin Heilmann, Duesseldorf (DE); Axel Trautwein, Duesseldorf (DE); Joerg Greul, Leverkusen (DE); Johannes-Rudolf Jansen, Monheim (DE); Udo Reckmann, Frankfurt a.M. (DE); Stefan Herrmann, Langenfeld (DE); Peter Loesel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 52 days.

This patent is subject to a terminal disclaimer.

(21) Appl. No.: 15/129,601

(22) PCT Filed: Mar. 27, 2015

(86) PCT No.: PCT/EP2015/056703
§ 371 (c)(1),
(2) Date: Sep. 27, 2016

(87) PCT Pub. No.: WO2015/150252
PCT Pub. Date: Oct. 8, 2015

(65) Prior Publication Data
US 2017/0135346 A1 May 18, 2017

(30) Foreign Application Priority Data

Apr. 1, 2014 (EP) .................................... 14163045

(51) Int. Cl.
| | |
|---|---|
| *A01N 43/56* | (2006.01) |
| *A01N 43/60* | (2006.01) |
| *C07D 403/04* | (2006.01) |
| *C07D 231/40* | (2006.01) |
| *C07D 401/04* | (2006.01) |
| *A01N 43/647* | (2006.01) |

(52) U.S. Cl.
CPC ............. *A01N 43/56* (2013.01); *A01N 43/60* (2013.01); *A01N 43/647* (2013.01); *C07D 231/40* (2013.01); *C07D 401/04* (2013.01); *C07D 403/04* (2013.01)

(58) Field of Classification Search
None
See application file for complete search history.

(56) References Cited

U.S. PATENT DOCUMENTS

| | | | |
|---|---|---|---|
| 9,802,899 B2 * | 10/2017 | Heilmann | A01N 43/653 |
| 2015/0239847 A1 | 8/2015 | Heilmann et al. | |
| 2017/0188581 A1 * | 7/2017 | Decor | A01N 43/647 |
| 2017/0305864 A1 * | 10/2017 | Heilmann | A01N 43/653 |

FOREIGN PATENT DOCUMENTS

| | | |
|---|---|---|
| WO | 2004018438 A2 | 3/2004 |
| WO | 2014053450 A1 | 4/2014 |
| WO | WO2015144652 | * 10/2015 |

OTHER PUBLICATIONS

D'Anna F et al: "On the application of the extended Fujita-Nishioka equation to polysubstituted systems". Tetrahedron, Vo. 61, No. 1, pp. 167-178, XP004658759.
Alberti Tironi: "Formazione di Amidi Sostituite per Ossidazione di Basi di Schiff Pirazoliche e Pirazoliniche". Farmaco, vol. 17, No. 6, pp. 468-480, XP009178390.
International Search Report of PCT/EP2015/056703 dated May 6, 2015.

* cited by examiner

*Primary Examiner* — Po-Chih Chen
(74) *Attorney, Agent, or Firm* — McBee Moore Woodward & Vanik IP, LLC

(57) ABSTRACT

The present invention relates generally to the use of heterocyclic compounds of the formula (I)

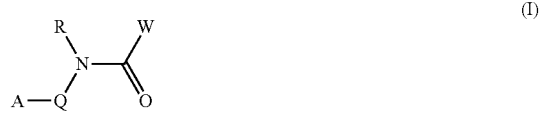

for controlling nematodes and to methods useful for controlling nematodes and/or increasing crop yield.

25 Claims, No Drawings

USE OF HETEROCYCLIC COMPOUNDS FOR CONTROLLING NEMATODES

CROSS REFERENCE TO RELATED APPLICATIONS

This application is a § 371 National State Application of PCT/EP2015/056703, filed Mar. 27, 2015, which claims priority to European Application No. 14163045.9 filed Apr. 1, 2014.

BACKGROUND OF THE INVENTION

Field of the Invention

The present invention relates to the use of compounds of formula (I) and compositions comprising compounds of formula (I) for controlling nematodes in various crops including vegetables, eg tomato, sweet peppers and cucurbits, potato, corn, soy, cotton, tobacco, coffee, fruits, e.g. citrus fruits, pine apples and bananas, and grapes and to methods particularly useful for controlling nematodes and/or increasing crop yield in various crops including vegetables, e.g. tomato, sweet peppers and cucurbits, potato, pepper, carrots, onions, corn, soy, cotton, tobacco, coffee, sugarcane, fruits, e.g. citrus fruits, pine apples and bananas, and grapes, tree crops—pome fruits, tree crops—stone fruits, tree crops—nuts, and flowers.

Description of Related Art

Nematodes are tiny, worm-like, multicellular animals adapted to living in water. The number of nematode species is estimated at half a million An important part of the soil fauna, nematodes live in a maze of interconnected channels, called pores, that are formed by soil processes. They move in the films of water that cling to soil particles. Plant-parasitic nematodes, a majority of which are root feeders, are found in association with most plants. Some are endoparasitic, living and feeding within the tissue of the roots, tubers, buds, seeds, leaves etc. Others are ectoparasitic, feeding externally through plant walls. A single endoparasitic nematode can kill a plant or reduce its productivity. Endoparasitic root feeders include such economically important pests as the root-knot nematodes (*Meloidogyne* species), the reniform nematodes (*Rotylenchulus* species), the cyst nematodes (*Heterodera* species), and the root-lesion nematodes (*Pratylenchus* species). Direct feeding by nematodes can drastically decrease a plant's uptake of nutrients and water. Nematodes have the greatest impact on crop productivity when they attack the roots of seedlings immediately after seed germination or transplanting. Nematode feeding also creates open wounds that provide entry to a wide variety of plant-pathogenic fungi and bacteria. These microbial infections are often more economically damaging than the direct effects of nematode feeding.

Current nematode control focuses essentially on the prevention of nematode attack on the plant. Once a plant is parasitized it is virtually impossible to kill the nematode without also destroying the plant. Therefore, it would be advantageous to provide nematode control compounds and methods of treating plants to prevent or reduce nematode damage.

SUMMARY

This invention now provides the use of compounds of formula (I)

(I)

A-1

A-2

A-3

Q-1

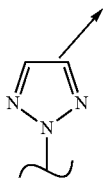

Q-2 in which A is A-1 or A-2 or A-3 in which the dotted line represents the bond to the N atom of Q, Q is Q-1 or Q-2 in which the nitrogen is attached to ring A and the arrow in each case represents the bond to the NRCO moiety, R is H or ethyl and W represents a radical from the group consisting of W-1 to W-3

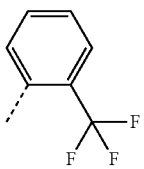

W-1

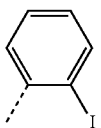

W-2

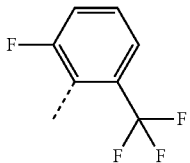

W-3 in which the dotted line represents the bond to the C=O group, for controlling nematodes infesting crops selected from the group consisting of vegetables, in particular fruity vegetables, e.g. sweet peppers, melons, egg plants, tomato and cucurbits, potato, pepper, carrots, onions, corn, soy, cotton, tobacco, coffee, sugarcane, fruits e.g. citrus fruits, pine apples and bananas, and grapes, tree crops—pome fruits, tree crops—stone fruits, tree crops—nuts, flowers and/or for increasing yield.

DETAILED DESCRIPTION OF A PREFERRED EMBODIMENT

In one embodiment the invention is directed to the use of a compound of formula (I-1) as listed in Table 1

TABLE 1

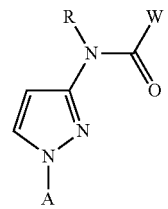

(I-1)

| Compound No. | A | W | R |
|---|---|---|---|
| I-1-75 | 2,6-difluorophenyl (A-1) | 2-(trifluoromethyl)phenyl (W-1) | H |
| I-1-83 | 2,6-difluorophenyl (A-1) | 2-iodophenyl (W-2) | H |
| I-1-140 | 3,5-difluoro-pyridin-2-yl (A-2) | 2-(trifluoromethyl)phenyl (W-1) | H |
| I-1-468 | 3,5-difluoro-pyridin-2-yl (A-2) | 2-(trifluoromethyl)phenyl (W-1) | ethyl |
| I-1-574 | 3-cyanopyrazin-2-yl (A-3) | 2-(trifluoromethyl)phenyl (W-1) | H |

In another embodiment the invention is directed to the use of a compound of formula (I-2) as listed in Table 2

TABLE 2

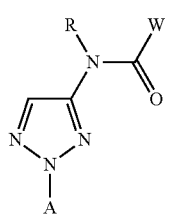

(I-2)

| Compound No. | A | W | R |
|---|---|---|---|
| I-2-35 | 2,6-difluorophenyl (A-1) | 2-(trifluoromethyl)phenyl (W-1) | H |
| I-2-66 | 3,5-difluoropyridin-2-yl (A-2) | 2-(trifluoromethyl)phenyl (W-1) | H |
| I-2-71 | 3,5-difluoropyridin-2-yl (A-2) | 2-fluoro-6-(trifluormethyl)phenyl (W-3) | H |

Compounds of formula (I) and their use for controlling nematodes and animal pests are disclosed with their compound numbers in WO 2014/053450. In one biological example the efficacy of selected compounds of formula (I) against *Meloidogyne incognita* in lettuce is described.

The invention relates further to the use of compounds of formula (I) for controlling nematodes selected from the group of genera selected from *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp, *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp. infesting crops selected from the group consisting of vegetables, in particular tomato, peppers, melons, eggplants, and cucurbits, potato, corn, soy, cotton, tobacco, coffee, fruits, in particular, citrus fruits, pine apples and bananas, and grapes.

The invention relates further to the use of compounds of formula (I) for controlling nematodes selected from the group of genera selected from *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus* spp., *Trichodorus* spp., *Tylenchulus* spp, *Xiphinema* spp., *Helicotylenchus* spp., *Tylenchorhynchus* spp., *Scutellonema* spp., *Paratrichodorus* spp., *Meloinema* spp., *Paraphelenchus* spp., *Aglenchus* spp., *Belonolaimus* spp., *Nacobbus* spp, *Rotylenchulus* spp., *Rotylenchus* spp., *Neotylenchus* spp., *Paraphelenchus* spp., *Dolichodorus* spp., *Hoplolaimus* spp., *Punctodera* spp., *Criconemella* spp., *Quinisulcius* spp., *Hemicycliophora* spp., *Anguina* spp., *Subanguina* spp., *Hemicriconemoides* spp., *Psilenchus* spp., *Pseudohalenchus* spp., *Criconemoides* spp., *Cacopaurus* spp. infesting crops selected from the group consisting of vegetables, in particular tomato and cucurbits, potato, pepper, carrots, onions, corn, soy, cotton, tobacco, coffee, sugarcane, fruits, in particular, citrus fruits, pine apples and bananas, and grapes, tree crops—pome fruits, tree crops—stone fruits, tree crops—nuts, flowers and/or for increasing yield.

The invention relates further to the use of compounds of formula (I) for controlling nematode species selected from the group consisting of *Aglenchus agricola, Anguina tritici, Aphelenchoides arachidis, Aphelenchoides fragariae, Belonolaimus gracilis, Belonolaimus longicaudatus, Belonolaimus nortoni, Cacopaurus pestis, Criconemella curvata, Criconemella onoensis, Criconemella ornata, Criconemella rusium, Criconemella xenoplax* (=*Mesocriconema xenoplax*) and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and *Ditylenchus* spp. in general, *Dolichodorus heterocephalus, Globodera pallida* (=*Heterodera pallida*), *Globodera rostochiensis, Globodera solanacearum, Globodera tabacum, Globodera virginiae, Helicotylenchus digonicus, Helicotylenchus dihystera, Helicotylenchus erythrine, Helicotylenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines, Heterodera oryzae, Heterodera schachtii, Heterodera zeae* and *Heterodera* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne naasi, Meloidogyne paranaensis, Meloidogyne thamesi* and *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis, Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and *Trichodorus* spp. in general, *Tylenchorhynchus agri, Tylenchorhynchus brassicae, Tylenchorhynchus clams, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans, Xiphinema americanum, Xiphinema brevicolle, Xiphinema dimorphicaudatum, Xiphinema index* and *Xiphinema* spp. in general.

An exemplary method of the invention comprises applying compounds of formula (I) of the invention to either soil or a plant (e.g., foliarly) to control nematode damage and/or increase crop yield.

Vegetables are for example broccoli, cauliflower, globe artichokes, Sweet corn (maize), peas, beans, kale, collard greens, spinach, arugula, beet greens, bok choy, chard, choi sum, turnip greens, mustard greens, watercress, garlic chives, gai lan, leeks, brussels sprouts, capers, kohlrabi, celery, rhubarb, cardoon, Chinese celery, lemon grass, asparagus, bamboo shoots, galangal, and ginger, potatoes, Jerusalem artichokes, sweet potatoes, taro, yams soybean sprouts, mung beans, urad, alfalfa, carrots, parsnips, beets, radishes, rutabagas, turnips, burdocks, onions, shallots, garlic, tomatoes, curcurbits (cucumbers, squash, pumpkins, melons, luffas, gourds, watermelons), zucchinis, sweet peppers, eggplant, tomatillos, christophene, okra, breadfruit and avocado, green beans, lentils, snow peas.

Preferred vegetables are fruity vegetables e.g. tomato, pepper, eggplant, cucurbits e.g. melon, zucchini, cucumber, pumkin, potato, carrots, onions, Tree crops—stone fruits are e.g. apricots, cherries, almonds and peaches.

Tree crops—pome fruits are e.g. apples, pears.

Tree crops—nuts are e.g. Beech, Brazil nut, Candlenut, Cashew, Chestnuts, including Chinese Chestnut, Sweet Chestnut, Colocynth, *Cucurbita ficifolia*, Filbert, *Gevuina avellana*, Hickory, including Pecan, Shagbark Hickory, *Terminalia catappa*, Hazelnut, Indian Beech, Kola nut, Macadamia, Malabar chestnut, *Pistacia*, Mamoncillo, Maya nut, Mongongo, Oak acorns, Ogbono nut, Paradise nut, Pili nut, Walnut, Black Walnut, Water Caltrop, Mango, Lychee.

In conjunction with the present invention "controlling" denotes a preventive or curative reduction of the nematode infestation in comparison to the untreated crop, more preferably the infestation is essentially repelled, most preferably the infestation is totally suppressed.

Pathosystems

Compounds of formula (I) are particularly useful in controlling nematodes in coffee belonging to at least one species selected from the group of the phytoparasitic nematodes consisting of *Pratylenchus brachyurus, Pratylenchus coffeae, Meloidogyne exigua, Meloidogyne incognita, Meloidogyne coffeicola, Helicotylenchus* spp. and also consisting of *Meloidogyne paranaensis, Rotylenchus* spp., *Xiphinema* spp., *Tylenchorhynchus* spp., *Scutellonema* spp.

Compounds of formula (I) are particularly useful in controlling nematodes in potato belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compounds of formula (I) are particularly useful in controlling nematodes in tomato belonging to at least one species selected from the group of the phytoparasitic nematodes consisting of *Meloidogyne arenaria, Meloidogyne hapla, Meloidogyne javanica, Meloidogyne incognita, Pratylenchus penetrans* and also consisting of *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus, Rotylenchulus reniformis*.

Compounds of formula (I) are particularly useful in controlling nematodes in sweet peppers belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compounds of formula (I) are particularly useful in controlling nematodes in carrots belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compounds of formula (I) are particularly useful in controlling nematodes in onions belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compounds of formula (I) are particularly useful in controlling nematodes in cucurbits belonging to at least one species selected from the group of the phytoparasitic nematodes consisting of *Meloidogyne arenaria, Meloidogyne hapla, Meloidogyne javanica, Meloidogyne incognita, Rotylenchulus reniformis* and also consisting of *Pratylenchus thornei*.

Compounds of formula (I) are particularly useful in controlling nematodes in cucurbits belonging to at least one species selected from the group of the phytoparasitic nematodes consisting of *Meloidogyne arenaria, Meloidogyne hapla, Meloidogyne javanica, Rotylenchulus reniformis* and also consisting of *Pratylenchus thornei*.

Compounds of formula (I) are particularly useful in controlling nematodes in cotton belonging to at least one species selected from the group of the phytoparasitic nematodes consisting of *Belonolaimus longicaudatus, Meloidogyne incognita, Hoplolaimus columbus, Hoplolaimus galeatus, Rotylenchulus reniformis*.

Compounds of formula (I) are particularly useful in controlling nematodes in corn belonging to at least one species selected from the group of the phytoparasitic nematodes, especially consisting of *Belonolaimus longicaudatus, Paratrichodorus minor* and also consisting of *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyumm, Subanguina radiciola*.

Compounds of formula (I) are particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Heterodera glycines, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis*.

Compounds of formula (I) are very particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis*.

Compounds of formula (I) are particularly useful in controlling nematodes in tobacco belonging to at least one species selected from the group of the phytoparasitic nematodes, especially consisting of *Meloidogyne incognita, Meloidogyne javanica* and also consisting of *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus spp., Meloidogyne arenaria, Meloidogyne hapla, Globodera tabacum, Globodera solanacearum, Globodera virginiae, Ditylenchus dipsaci, Rotylenchus spp., Helicotylenchus spp., Xiphinema americanum, Criconemella spp., Rotylenchulus reniformis, Tylenchorhynchus claytoni, Paratylenchus spp., Tetylenchus nicotianae*.

Compounds of formula (I) are particularly useful in controlling nematodes in citrus belonging to at least one species selected from the group of the phytoparasitic nematodes, especially consisting of *Pratylenchus coffeae* and also consisting of *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella spp., Hemicriconemoides, (Radopholus similis), Radopholus citrophilus, Hemicycliophora arenaria, Hemicycliophora nudata, Tylenchulus semipenetrans*.

Compounds of formula (I) are particularly useful in controlling nematodes in banana belonging to at least one species selected from the group of the phytoparasitic nematodes, especially consisting of *Pratylenchus coffeae, Radopholus similis* and also consisting of *Pratylenchus giibbicaudatus, Pratylenchus loosi, Meloidogyne spp., Helicotylenchus multicinctus, Helicotylenchus dihystera, Rotylenchulus spp*.

Compounds of formula (I) are particularly useful in controlling nematodes in pine apple belonging to at least one species selected from the group of the phytoparasitic nematodes, especially consisting of *Pratylenchus zeae, Pratylenchus pratensis, Pratylenchus brachyurus, Pratylenchus goodeyi., Meloidogyne spp., Rotylenchulus reniformis* and also consisting of *Longidorus elongatus, Longidorus laevicapitatus, Trichodorus primitivus, Trichodorus minor, Heterodera spp., Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense, Criconemoides ornatum*.

Compounds of formula (I) are particularly useful in controlling nematodes in sugarcane belonging to at least one species selected from the group of the phytoparasitic nematodes, especially consisting of *Pratylenchus brachyurus, Pratylenchus pratensis, Pratylenchus scribneri, Pratylenchus penetrans, Pratylenchus coffeae, Ditylenchus dipsaci* and also consisting of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Meloidogyne arenaria, Meloidogyne acronea, Meloidogyne artiella, Meloidogyne incognita, Meloidogyne graminicola, Meloidogyne javanica, Meloidogyne thamesi, Meloidogyne hapla, Meloidogyne ethiopica, Meloidogyne africana, Meloidogyne kikuyensis, Helicotylenchus digonicus, Helicotylenchus dihystera, Helicotylen-*

*chus pseudorobustus, Rotylenchulus borealis, Rotylenchulus parvus, Rotylenchulus reniformis, Scutellonema brachyurum.*

Compounds of formula (I) are particularly useful in controlling nematodes in grapes belonging to at least one species selected from the group of the phytoparasitic nematodes, especially consisting of *Pratylenchus vulnus, Meloidogyne arenaria, Meloidogyne incognita, Meloidogyne javanica, Xiphinema americanum, Xiphinema index* and also consisting of *Pratylenchus pratensis, Pratylenchus scribneri, Pratylenchus neglectus, Pratylenchus brachyurus, Pratylenchus thornei, Tylenchulus semipenetrans.*

Compounds of formula (I) are particularly useful in controlling nematodes in tree crops—pome fruits, belonging to at least one species selected from the group of the phytoparasitic nematodes, especially consisting of *Pratylenchus penetrans* and also consisting of *Pratylenchus vulnus, Longidorus elongatus, Meloidogyne incognita, Meloidogyne hapla.*

Compounds of formula (I) are particularly useful in controlling nematodes in tree crops—stone fruits, belonging to at least one species selected from the group of the phytoparasitic nematodes, especially consisting of *Pratylenchus penetrans, Pratylenchus vulnus, Meloidogyne arenaria, Meloidogyne hapla, Meloidogyne javanica, Meloidogyne incognita, Criconemella* xenoplax and also consisting of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum, Hoplolaimus galeatus.*

Compounds of formula (I) are particularly useful in controlling nematodes in tree crops—nuts, belonging to at least one species selected from the group of the phytoparasitic nematodes, especially consisting of *Trichodorus* spp., *Criconemella rusium* and also consisting of *Pratylenchus vulnus, Paratrichodorus* spp., *Meloidogyne incognita, Helicotylenchus* spp., *Tylenchorhynchus* spp., *Cacopaurus pestis.*

Definition of Plant Parts

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, tubers, corms and rhizomes are listed. Crops and vegetative and generative propagating material, for example cuttings, corms, rhizomes, tubers, runners and seeds also belong to plant parts.

As already mentioned above, it is possible to treat all plants and their parts according to the invention. In one embodiment, wild plant species and plant cultivars, or those obtained by conventional biological breeding, such as crossing or protoplast fusion, and parts thereof, are treated. In a further embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

GMOs

Plants of the plant cultivars which are in each case commercially available or in use can be treated according to the invention. Plant cultivars are to be understood as meaning plants having novel properties ("traits") which can be obtained by conventional breeding, by mutagenesis or by recombinant DNA techniques. This can be varieties, bio- and genotypes.

The transgenic plants or plant cultivars (i.e. those obtained by genetic engineering) which can be treated according to the invention include all plants which, in the genetic modification, received genetic material which imparted particularly advantageous useful traits to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against nematodes, insects, mites, phytopathogenic fungi, bacteria and/or viruses, and also increased tolerance of the plants to certain herbicidal active compounds. Particular emphasis is given to vegetables, in particular tomato and cucurbits, potato, corn, soy, cotton, tobacco, coffee, fruits, in particular citrus fruits, pine apples and bananas, and grapes.

The method of treatment according to the invention can be used in the treatment of genetically modified organisms (GMOs), e.g. plants. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a *Petunia* EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364, 724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646, 024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases HPPD is an are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at:
http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at:
http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549 b) Plants, such as cotton plants, containing an altered form of rsw2 or rsw3 homologous nucleic acids as described in WO 2004/053219 c) Plants, such as cotton plants, with increased expression of sucrose phosphate synthase as described in WO 01/17333 d) Plants, such as cotton plants, with increased expression of sucrose synthase as described in WO 02/45485 e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947 b) Plants such as oilseed rape plants, producing oil having a low linolenic acid content as described in U.S. Pat. Nos. 6,270,828, 6,169,190, or 5,965,755 c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as potatoes which are virus-resistant, e.g. against potato virus Y (event SY230 and SY233 from Tecnoplant, Argentina), which are disease resistant, e.g. against potato late blight (e.g. RB gene), which show a reduction in cold-induced sweetening (carrying the Nt-Inhh, IIR-INV gene) or which possess a dwarf phenotype (Gene A-20 oxidase).

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

The present invention relates also to the use of compounds of formula (I) for controlling nematodes in plants containing transformation events, or a combination of transformation events, and that are listed for example in the databases for various national or regional regulatory agencies including Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US2002120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control—herbicide tolerance, deposited as PTA-6233, described in WO2005/103266 or US2005216969); Event 3006-210-23 (cotton, insect control—herbicide tolerance, deposited as PTA-6233, described in US2007143876 or WO2005/103266); Event 3272 (corn, quality trait, deposited as PTA-9972, described in WO2006098952 or US2006230473); Event 40416 (corn, insect control—herbicide tolerance, deposited as ATCC PTA-11508, described in WO2011/075593); Event 43A47 (corn, insect control—herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US2006162007 or WO2004053062); Event B16 (corn, herbicide tolerance, not deposited, described in US2003126634); Event BPS-CV127-9 (soybean, herbicide tolerance, deposited as NCIMB No. 41603, described in WO2010/080829); Event CE43-67B (cotton, insect control, deposited as DSM ACC2724, described in US2009217423 or WO2006/128573); Event CE44-69D (cotton, insect control, not deposited, described in US20100024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US2006130175 or WO2004039986); Event COT202 (cotton, insect control, not deposited, described in US2007067868 or WO2005054479); Event COT203 (cotton, insect control, not deposited, described in WO2005/054480); Event DAS40278 (corn, herbicide tolerance, deposited as ATCC PTA-10244, described in WO2011/022469); Event DAS-59122-7 (corn, insect control—herbicide tolerance, deposited as ATCC PTA 11384, described in US2006070139); Event DAS-59132 (corn, insect control—herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US2009137395 or WO2008/112019); Event DP-305423-1 (soybean, quality trait, not deposited, described in US2008312082 or WO2008/054747); Event DP-32138-1 (corn, hybridization system, deposited as ATCC PTA-9158, described in US20090210970 or WO2009/103049); Event DP-356043-5 (soybean, herbicide tolerance, deposited as ATCC PTA-8287, described in US20100184079 or WO2008/002872); Event EE-1 (brinjal, insect control, not deposited, described in WO2007/091277); Event FI117 (corn, herbicide tolerance, deposited as ATCC 209031, described in US2006059581 or WO1998/044140); Event GA21 (corn, herbicide tolerance, deposited as ATCC 209033, described in US2005086719 or WO1998/044140); Event GG25 (corn, herbicide tolerance, deposited as ATCC 209032, described in US2005188434 or WO1998/044140); Event GHB119 (cotton, insect control—herbicide tolerance, deposited as ATCC PTA-8398, described in WO2008/151780); Event GHB614 (cotton, herbicide tolerance, deposited as ATCC PTA-6878, described in US2010050282 or WO2007/017186); Event GM (corn, herbicide tolerance, deposited as ATCC 209030, described in US2005188434 or WO1998/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US2004172669 or WO2004/074492); Event JOPLIN1 (wheat, disease tolerance, not deposited, described in US2008064032); Event LL27 (soybean, herbicide tolerance, deposited as NCIMB41658, described in WO2006/108674 or US2008320616); Event LL55 (soybean, herbicide tolerance, deposited as NCIMB 41660, described in WO2006/108675 or US2008196127); Event LLcotton25 (cotton, herbicide tolerance, deposited as ATCC PTA-3343, described in WO2003013224 or US2003097687); Event LLRICE06 (rice, herbicide tolerance, deposited as ATCC-23352, described in U.S. Pat. No. 6,468,747 or WO2000/026345); Event LLRICE601 (rice, herbicide tolerance, deposited as ATCC PTA-2600, described in US20082289060 or WO2000/026356); Event LY038 (corn, quality trait, deposited as ATCC PTA-5623, described in US2007028322 or WO2005061720); Event MIR162 (corn, insect control, deposited as PTA-8166, described in US2009300784 or WO2007/142840); Event MIR604 (corn, insect control, not deposited, described in US2008167456 or WO2005103301); Event MON15985 (cotton, insect control, deposited as ATCC PTA-2516, described in US2004-250317 or WO2002/100163); Event MON810 (corn, insect control, not deposited, described in US2002102582); Event MON863 (corn, insect control, deposited as ATCC PTA-2605, described in WO2004/011601 or US2006095986); Event MON87427 (corn, pollination control, deposited as ATCC PTA-7899, described in WO2011/062904); Event MON87460 (corn, stress tolerance, deposited as ATCC PTA-8910, described in WO2009/111263 or US20110138504); Event MON87701 (soybean, insect control, deposited as ATCC PTA-8194, described in US2009130071 or WO2009/064652); Event MON87705 (soybean, quality trait—herbicide tolerance, deposited as ATCC PTA-9241, described in US20100080887 or WO2010/037016); Event MON87708 (soybean, herbicide tolerance, deposited as ATCC PTA9670, described in WO2011/034704); Event MON87754 (soybean, quality trait, deposited as ATCC PTA-9385, described in WO2010/024976); Event MON87769 (soybean, quality trait, deposited as ATCC PTA-8911, described in US20110067141 or WO2009/102873); Event MON88017 (corn, insect control—herbicide tolerance, deposited as ATCC PTA-5582, described in US2008028482 or WO2005/059103); Event MON88913 (cotton, herbicide tolerance, deposited as ATCC PTA-4854, described in WO2004/072235 or US2006059590); Event MON89034 (corn, insect control, deposited as ATCC PTA-7455, described in WO2007/140256 or US2008260932); Event MON89788 (soybean, herbicide tolerance, deposited as ATCC PTA-6708, described in US2006282915 or WO2006/130436); Event MS11 (oilseed rape, pollination control—herbicide tolerance, deposited as ATCC PTA-850 or PTA-2485, described in WO2001/031042); Event MS8 (oilseed rape, pollination control—herbicide tolerance, deposited as ATCC PTA-730, described in WO2001/041558 or US2003188347); Event NK603 (corn, herbicide tolerance, deposited as ATCC PTA-2478, described in US2007-292854); Event PE-7 (rice, insect control, not deposited, described in WO2008/114282); Event RF3 (oilseed rape, pollination control—herbicide tolerance, deposited as ATCC PTA-730, described in WO2001/041558 or US2003188347); Event RT73 (oilseed rape, herbicide tolerance, not deposited, described in WO2002/036831 or US2008070260); Event T227-1 (sugar beet, herbicide tolerance, not deposited, described in WO2002/44407 or US2009265817); Event T25 (corn, herbicide tolerance, not deposited, described in US2001029014 or WO2001/051654); Event T304-40 (cotton, insect control—herbicide tolerance, deposited as ATCC PTA-8171, described in US2010077501 or WO2008/122406); Event T342-142 (cotton, insect control, not deposited, described in WO2006/128568); Event TC1507 (corn, insect control—herbicide tolerance, not deposited, described in US2005039226 or WO2004/099447); Event VIP1034 (corn, insect control—herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621).

The present invention relates also to the use of compounds of formula (I) for controlling nematodes in plants carrying the one or more of the events listed in Table A below:

TABLE A

| | Event | Company | Description |
|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 |
| A-2 | GM RZ13 | | Beet Necrotic Yellow Vein Virus (BNYVV) resistance |
| A-3 | H7-1 | Monsanto Company | Glyphosate herbicide tolerant sugar beet produced by inserting a gene encoding the enzyme 5-enolypyruvylshikimate-3-phosphate synthase (EPSPS) from the CP4 strain of *Agrobacterium tumefaciens*,; WO 2004-074492 |
| A-4 | T120-7 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| A-5 | GTSB77 | Novartis Seeds; Monsanto Company | Glyphosate herbicide tolerant sugar beet produced by inserting a gene encoding the enzyme 5-enolpyruvylshikimate-3-phosphate synthase (EPSPS) from the CP4 strain of *Agrobacterium tumefaciens*. |

TABLE A-continued

| | | | |
|---|---|---|---|
| A-6 | T227-1 | | Glyphosate tolerance; US 2004-117870 |
| A-7 | 23-18-17, 23-198 | Monsanto Company (formerly Calgene) | High laurate (12:0) and myristate (14:0) canola produced by inserting a thioesterase encoding gene from the California bay laurel (*Umbellularia californica*). |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. |
| A-9 | 46A12, 46A16 | Pioneer Hi-Bred International Inc. | Combination of chemical mutagenesis, to achieve the high oleic acid trait, and traditional breeding with registered canola varieties. |
| A-10 | GT200 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. |
| A-11 | GT73, RT73 | Monsanto Company | Glyphosate herbicide tolerant canola produced by inserting genes encoding the enzymes 5-enolypyruvylshikimate-3-phosphate synthase (EPSPS) from the CP4 strain of *Agrobacterium tumefaciens* and glyphosate oxidase from *Ochrobactrum anthropi*. |
| A-12 | HCN10 | Aventis CropScience | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| A-13 | HCN92 | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| A-14 | MS1, RF1 =>PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |
| A-15 | MS1, RF2 =>PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |
| A-16 | MS8×RF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacteria, and both lines contained the phosphinothricin N-acetyltransferase (PAT) encoding gene from *Streptomyces hygroscopicus*. |
| A-17 | MS-B2 | | Male sterility; WO 01/31042 |
| A-18 | MS-BN1/RF-BN1 | | Male sterility/restoration; WO 01/41558 |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. |
| A-20 | OXY-235 | Aventis CropScience (formerly Rhone Poulenc Inc.) | Tolerance to the herbicides bromoxynil and ioxynil by incorporation of the nitrilase gene from *Klebsiella pneumoniae*. |
| A-21 | PHY14, PHY35 | Aventis CropScience (formerly Plant Genetic Systems) | Male sterility was via insertion of the barnase ribonuclease gene from *Bacillus amyloliquefaciens*; fertility restoration by insertion of the barstar RNase inhibitor; PPT resistance was |

TABLE A-continued

| | | | |
|---|---|---|---|
| A-22 | PHY36 | Aventis CropScience (formerly Plant Genetic Systems) | via PPT-acetyltransferase (PAT) from *Streptomyces hygroscopicus*.<br>Male sterility was via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. |
| A-23 | RT73 | | Glyphosate resistance; WO 02/36831 |
| A-24 | T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacteria. PPT normally acts to inhibit glutamine synthetase, causing a fatal accumulation of ammonia. Acetylated PPT is inactive. |
| A-25 | HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. |
| A-26 | ZSR500/502 | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by interspecific crossing with GT73. |
| A-27 | EE-1 | | Insect resistance (Cry1Ac) |
| A-28 | 55-1/63-1 | Cornell University | Papaya ringspot virus (PRSV) resistant papaya produced by inserting the coat protein (CP) encoding sequences from this plant potyvirus. |
| A-29 | X17-2 | University of Florida | Papaya ringspot virus (PRSV) resistant papaya produced by inserting the coat protein (CP) encoding sequences from PRSV isolate H1K with a thymidine inserted after the initiation codon to yield a frameshift. Also contains nptII as a selectable marker. |
| A-30 | RM3-3, RM3-4, RM3-6 | Bejo Zaden BV | Male sterility was via insertion of the barnase ribonuclease gene from *Bacillus amyloliquefaciens*; PPT resistance was via the bar gene from *S. hygroscopicus*, which encodes the PAT enzyme. |
| A-32 | A, B | Agritope Inc. | Reduced accumulation of S-adenosylmethionine (SAM), and consequently reduced ethylene synthesis, by introduction of the gene encoding S-adenosylmethionine hydrolase. |
| A-33 | CZW-3 | Asgrow (USA); Seminis Vegetable Inc. (Canada) | Cucumber mosiac virus (CMV), zucchini yellows mosaic (ZYMV) and watermelon mosaic virus (WMV) 2 resistant squash (*Curcurbita pepo*) produced by inserting the coat protein (CP) encoding sequences from each of these plant viruses into the host genome. |
| A-34 | ZW20 | Upjohn (USA); Seminis Vegetable Inc. (Canada) | Zucchini yellows mosaic (ZYMV) and watermelon mosaic virus (WMV) 2 resistant squash (*Curcurbita pepo*) produced by inserting the coat protein (CP) encoding sequences from each of these plant potyviruses into the host genome. |
| A-35 | 66 | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. |
| A-36 | 4, 11, 15, 16 | Florigene Pty Ltd. | Modified colour and sulfonylurea herbicide tolerant carnations produced by inserting two anthocyanin biosynthetic genes whose expression results in a violet/mauve colouration. Tolerance to sulfonyl urea herbicides was via the introduction of a chlorsulfuron tolerant version of the acetolactate synthase (ALS) encoding gene from tobacco. |

TABLE A-continued

| | | | |
|---|---|---|---|
| A-37 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). |
| A-38 | 3560.4.3.5 | | Glyphosate/ALS inhibitor-tolerance; WO 2008002872 |
| A-39 | A2704-12, A2704-21 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*.; WO 2006/108674 |
| A-40 | A5547-127 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| A-41 | A5547-35 | Bayer CropScience (Aventis CropScience(AgrEvo)) | Glufosinate tolerance; WO 2006/108675 |
| A-42 | DP-305423-1 | Pioneer Hi-Bred International Inc. | High oleic acid/ALS inhibitor tolerance; |
| A-43 | DP356043 | Pioneer Hi-Bred International Inc. | Soybean event with two herbicide tolerance genes: glyphosate N-acetlytransferase, which detoxifies glyphosate, and a modified acetolactate synthase (A |
| A-44 | G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. |
| A-45 | GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. |
| A-46 | GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. |
| A-47 | MON87701 | Monsanto Company | insect resistance (Cry1ac); WO 2009064652 |
| A-48 | MON87705 | Monsanto Company | altered fatty acid levels (mid-oleic and low saturate); WO 2010037016 |
| A-49 | MON87754 | Monsanto Company | increased oil content; |
| A-50 | MON87769 | Monsanto Company | stearidonic acid (SDA) comprising oil; |
| A-51 | MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4; |
| A-52 | MON89788, MON19788 | Monsanto Company | Glyphosate tolerance, WO2006130436 |
| A-53 | OT96-15 | Agriculture & Agri-Food Canada | Low linolenic acid soybean produced through traditional cross-breeding to incorporate the novel trait from a naturally occurring fan1 gene mutant that was selected for low linolenic acid. |
| A-54 | W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. |
| A-55 | 15985 | Monsanto Company | Insect resistant cotton derived by transformation of the DP50B parent variety, which contained event 531 (expressing Cry1Ac protein), with purified plasmid DNA containing the cry2Ab gene from *B. thuringiensis* subsp. *kurstaki*. |
| A-56 | 1143-14A | | Insect resistance (Cry1Ab) |
| A-57 | 1143-51B | | Insect resistance (Cry1Ab) |
| A-58 | 19-51A | DuPont Canada Agricultural Products | Introduction of a variant form of acetolactate synthase (ALS). |
| A-59 | 281-24-236 | DOW AgroSciences LLC | Insect-resistant cotton produced by inserting the cry1F gene from *Bacillus thuringiensis* var. *aizawai*. The PAT encoding gene from *Streptomyces viridochromogenes* was introduced as a selectable marker. |
| A-60 | 3006-210-23 | DOW AgroSciences LLC | Insect-resistant cotton produced by inserting the cry1Ac gene from *Bacillus thuringiensis* subsp. *kurstaki*. The PAT encoding gene from *Streptomyces viridochromogenes* was introduced as a selectable marker. |

TABLE A-continued

| | | | |
|---|---|---|---|
| A-61 | 31807/31808 | Calgene Inc. | Insect-resistant and bromoxynil herbicide tolerant cotton produced by inserting the cry1Ac gene from *Bacillus thuringiensis* and a nitrilase encoding gene from *Klebsiella pneumoniae*. |
| A-62 | BXN | Calgene Inc. | Bromoxynil herbicide tolerant cotton produced by inserting a nitrilase encoding gene from *Klebsiella pneumoniae*. |
| A-63 | CE43-67B | | Insect resistance (Cry1Ab) |
| A-64 | CE44-69D | | Insect resistance (Cry1Ab) |
| A-65 | CE46-02A | | Insect resistance (Cry1Ab) |
| A-66 | Cot102 | Syngenta Seeds, Inc. | Insect-resistant cotton produced by inserting the vip3A(a) gene from *Bacillus thuringiensis* AB88. The APH4 encoding gene from *E. coli* was introduced as a selectable marker.; |
| A-67 | COT202 | Syngenta Seeds, Inc. | Insect resistance (VIP3A) |
| A-68 | Cot202 | Syngenta Seeds, Inc. | Insect resistance (VIP3) |
| A-69 | Cot67B | Syngenta Seeds, Inc. | Insect-resistant cotton produced by inserting a full-length cry1Ab gene from *Bacillus thuringiensis*. The APH4 encoding gene from *E. coli* was introduced as a selectable marker. |
| A-70 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). |
| A-71 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). |
| A-72 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). |
| A-73 | EE-GH3 | | Glyphosate tolerance |
| A-74 | EE-GH5 | | Insect resistance (Cry1Ab) |
| A-75 | EE-GH6 | | Insect resistance (cry2Ae) |
| A-76 | event 281-24-236 | | Insect resistance (Cry1F) |
| A-77 | Event-1 | JK Agri Genetics Ltd (India) | Insect-resistant cotton produced by inserting the cry1Ac gene from *Bacillus thuringiensis* subsp. *kurstaki* HD-73 (B.t.k.). |
| A-78 | event3006-210-23 | | Insect resistance (Cry1Ac) |
| A-79 | GBH614 | Bayer CropScience (Aventis CropScience(AgrEvo)) | Glyphosate herbicide tolerant cotton produced by inserting 2mepsps gene into variety Coker312 by *Agrobacterium* under the control of Ph4a748At and TPotpC |
| A-80 | LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium *Streptomyces hygroscopicus*; WO 2003013224, WO 2007/017186 |
| A-81 | LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) |
| A-82 | MON 15985 | | Insect resistance (Cry1A/Cry2Ab) |
| A-83 | MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from *A. tumefaciens* strain CP4. |
| A-84 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: |

TABLE A-continued

| | | | |
|---|---|---|---|
| | | | MON-15985-7). Glyphosate tolerance is derived from MON88913 which contains two genes encoding the enzyme 5-enolypyruvylshikimate-3-phosphate synthase (EPSPS) from the CP4 strain of *Agrobacterium tumefaciens*. Insect resistance is derived MON15985 which was produced by transformation of the DP50B parent variety, which contained event 531 (expressing Cry1Ac protein), with purified plasmid DNA containing the cry2Ab gene from *B. thuringiensis* subsp. *kurstaki*. |
| A-85 | MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON1445 (OECD identifier: MON-Ø1445-2). |
| A-86 | MON531/757/1076 | Monsanto Company | Insect-resistant cotton produced by inserting the cry1Ac gene from *Bacillus thuringiensis* subsp. *kurstaki* HD-73 (B.t.k.). |
| A-87 | LLcotton25 | | Glufosinate resistance |
| A-88 | MON88913 | Monsanto Company | Glyphosate herbicide tolerant cotton produced by inserting two genes encoding the enzyme 5-enolypyruvylshikimate-3-phosphate synthase (EPSPS) from the CP4 strain of *Agrobacterium tumefaciens*,; WO 2004/072235 |
| A-89 | MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON1445 (OECD identifier: MON-Ø1445-2). |
| A-90 | PV-GHGT07 (1445) | | Glyphosate tolerance |
| A-91 | T304-40 | | Insect-resistance (Cry1Ab) |
| A-92 | T342-142 | | Insect resistance (Cry1Ab) |
| A-93 | X81359 | BASF Inc. | Tolerance to imidazolinone herbicides by selection of a naturally occurring mutant. |
| A-94 | RH44 | BASF Inc. | Selection for a mutagenized version of the enzyme acetohydroxyacid synthase (AHAS), also known as acetolactate synthase (ALS) or acetolactate pyruvate-lyase. |
| A-95 | FP967 | University of Saskatchewan, Crop Dev. Centre | A variant form of acetolactate synthase (ALS) was obtained from a chlorsulfuron tolerant line of *A. thaliana* and used to transform flax. |
| A-96 | 5345 | Monsanto Company | Resistance to lepidopteran pests through the introduction of the cry1Ac gene from *Bacillus thuringiensis* subsp. *Kurstaki*. |
| A-97 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. |
| A-98 | 1345-4 | DNA Plant Technology Corporation | Delayed ripening tomatoes produced by inserting an additional copy of a truncated gene encoding 1-aminocyclopropane-1-carboxyllic acid (ACC) synthase, which resulted in downregulation of the endogenous ACC synthase and reduced ethylene accumulation. |
| A-99 | 35 1 N | Agritope Inc. | Introduction of a gene sequence encoding the enzyme S-adenosylmethionine hydrolase that metabolizes the precursor of the fruit ripening hormone ethylene |
| A-100 | B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. |
| A-101 | FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. |
| A-102 | J101, J163 | Monsanto Company and Forage Genetics International | Glyphosate herbicide tolerant alfalfa (lucerne) produced by inserting a gene encoding the enzyme 5-enolypyruvylshikimate-3-phosphate synthase (EPSPS) from the CP4 strain of *Agrobacterium tumefaciens*. |

TABLE A-continued

| | | | |
|---|---|---|---|
| A-103 | C/F/93/08-02 | Societe National d'Exploitation des Tabacset Allumettes | Tolerance to the herbicides bromoxynil and ioxynil by incorporation of the nitrilase gene from *Klebsiella pneumoniae*. |
| A-104 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from *E. coli* was introduced as a selectable marker to identify transformants. |
| A-105 | CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). |
| A-106 | GAT-OS2 | | Glufosinate tolerance |
| A-107 | GAT-OS3 | | Glufosinate tolerance |
| A-108 | IMINTA-1, IMINTA-4 | BASF Inc. | Tolerance to imidazolinone herbicides induced by chemical mutagenesis of the acetolactate synthase (ALS) enzyme using sodium azide. |
| A-109 | LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*). |
| A-110 | LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*). |
| A-111 | PE-7 | | Insect resistance (Cry1Ac) |
| A-112 | PWC16 | BASF Inc. | Tolerance to the imidazolinone herbicide, imazethapyr, induced by chemical mutagenesis of the acetolactate synthase (ALS) enzyme using ethyl methanesulfonate (EMS). |
| A-113 | TT51 | | Insect resistance (Cry1Ab/Cry1Ac) |
| A-114 | C5 | United States Department of Agriculture - Agricultural Research Service | Plum pox virus (PPV) resistant plum tree produced through *Agrobacterium*-mediated transformation with a coat protein (CP) gene from the virus. |
| A-115 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). |
| A-116 | BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). |
| A-117 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. |
| A-118 | RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. |
| A-119 | EH92-527 | BASF Plant Science | Crop composition; Amflora; Unique EU identifier: BPS-25271-9 |
| A-120 | AP205CL | BASF Inc. | Selection for a mutagenized version of the enzyme acetohydroxyacid synthase (AHAS), also known as acetolactate synthase (ALS) or acetolactate pyruvate-lyase. |
| A-121 | AP602CL | BASF Inc. | Selection for a mutagenized version of the enzyme acetohydroxyacid synthase (AHAS), also known as acetolactate synthase (ALS) or acetolactate pyruvate-lyase. |
| A-122 | BW255-2, BW238-3 | BASF Inc. | Selection for a mutagenized version of the enzyme acetohydroxyacid synthase (AHAS), also known as acetolactate synthase (ALS) or acetolactate pyruvate-lyase. |
| A-123 | BW7 | BASF Inc. | Tolerance to imidazolinone herbicides induced by chemical mutagenesis of the acetohydroxyacid synthase (AHAS) gene using sodium azide. |
| A-124 | Event 1 | | *Fusarium* resistance (trichothecene 3-O-acetyltransferase); CA 2561992 |

TABLE A-continued

| | | | |
|---|---|---|---|
| A-125 | JOPLIN1 | | disease (fungal) resistance (trichothecene 3-O-acetyltransferase); US 2008064032 |
| A-126 | MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. |
| A-127 | SWP965001 | Cyanamid Crop Protection | Selection for a mutagenized version of the enzyme acetohydroxyacid synthase (AHAS), also known as acetolactate synthase (ALS) or acetolactate pyruvate-lyase. |
| A-128 | Teal 11A | BASF Inc. | Selection for a mutagenized version of the enzyme acetohydroxyacid synthase (AHAS), also known as acetolactate synthase (ALS) or acetolactate pyruvate-lyase. |
| A-129 | 176 | Syngenta Seeds, Inc. | Insect-resistant maize produced by inserting the cry1Ab gene from *Bacillus thuringiensis* subsp. *kurstaki*. The genetic modification affords resistance to attack by the European corn borer (ECB). |
| A-130 | 3272 | | Self processing corn (alpha-amylase) |
| A-131 | 3751IR | Pioneer Hi-Bred International Inc. | Selection of somaclonal variants by culture of embryos on imidazolinone containing media. |
| A-132 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. |
| A-133 | ACS-ZMØØ3-2 × MON-ØØ810-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ810-6). |
| A-134 | B16 | | Glufosinate resistance |
| A-135 | B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. |
| A-136 | BT11 (X4334CBR, X4734CBR) | Syngenta Seeds, Inc. | Insect-resistant and herbicide tolerant maize produced by inserting the cry1Ab gene from *Bacillus thuringiensis* subsp. *kurstaki*, and the phosphinothricin N-acetyltransferase (PAT) encoding gene from *S. viridochromogenes*. |
| A-137 | BT11 × GA21 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). |
| A-138 | BT11 × MIR162 | Syngenta Seeds, Inc. | Stacked insect resistant and herbicide tolerant maize produced by conventional cross breeding of parental lines BT11 (OECD unique identifier: SYN-BTØ11-1) and MIR162 (OECD unique identifier: SYN-IR162-4). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Resistance to other lepidopteran pests, including *H. zea*, *S. frugiperda*, *A. ipsilon*, and *S. albicosta*, is derived from MIR162, which contains the vip3Aa gene from *Bacillus thuringiensis* strain AB88. |
| A-139 | BT11 × MIR162 × MIR604 | Syngenta Seeds, Inc. | *Bacillus thuringiensis* Cry1Ab delta-endotoxin protein and the genetic material necessary for its production (via elements of vector pZO1502) in Event Bt11 corn (OECD Unique Identifier: SYN-BTØ11-1) × *Bacillus thuringiensis* Vip3Aa20 insecticidal protein and the genetic material necessary for its production (via elements of vector pNOV1300) in Event MIR162 maize (OECD Unique Identifier: SYN-IR162-4) × modified Cry3A protein and the genetic material necessary for its production (via elements of vector pZM26) in Event MIR604 corn (OECD Unique Identifier: SYN-IR6Ø4-5). |

TABLE A-continued

| | | | |
|---|---|---|---|
| A-140 | BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. |
| A-141 | BT11 × MIR604 × GA21 | Syngenta Seeds, Inc. | Stacked insect resistant and herbicide tolerant maize produced by conventional cross breeding of parental lines BT11 (OECD unique identifier: SYN-BTØ11-1), MIR604 (OECD unique identifier: SYN-IR6Ø5-5) and GA21 (OECD unique identifier: MON-ØØØ21-9). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbcicide is derived from GA21 which contains a a modified EPSPS gene from maize |
| A-142 | CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. |
| A-143 | DAS-06275-8 | DOW AgroSciences LLC | Lepidopteran insect resistant and glufosinate ammonium herbicide-tolerant maize variety produced by inserting the cry1F gene from *Bacillus thuringiensis* var *aizawai* and the phosphinothricin acetyltransferase (PAT) from *Streptomyces hygroscopicus*. |
| A-144 | DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker; US 2006-070139 |
| A-145 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Tolerance to glyphosate herbcicide is derived from NK603. |
| A-146 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from DAS-59122-7 which contains the cry34Ab1 and cry35Ab1 genes from *Bacillus thuringiensis* strain PS149B1. Lepidopteran resistance and toleraance to glufosinate ammonium herbicide is derived from TC1507. Tolerance to glyphosate herbcicide is derived from NK603. |
| A-147 | DAS-Ø15Ø7-1 × MON-ØØ6Ø3-6 | DOW AgroSciences LLC | Stacked insect resistant and herbicide tolerant corn hybrid derived from conventional cross-breeding of the parental lines 1507 (OECD identifier: DAS-Ø15Ø7-1) and NK603 (OECD identifier: MON-ØØ6Ø3-6). |
| A-148 | DBT418 | Dekalb Genetics Corporation | Insect-resistant and glufosinate ammonium herbicide tolerant maize developed by inserting genes encoding Cry1AC protein from *Bacillus* |

TABLE A-continued

| | | | |
|---|---|---|---|
| A-149 | DK404SR | BASF Inc. | *thuringiensis* subsp *kurstaki* and phosphinothricin acetyltransferase (PAT) from *Streptomyces hygroscopicus*<br>Somaclonal variants with a modified acetyl-CoA-carboxylase (ACCase) were selected by culture of embryos on sethoxydim enriched medium. |
| A-150 | DP-098140-6 | | Glyphosate tolerance/ALS inhibitor tolerance |
| A-151 | DP-Ø98140-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. |
| A-152 | Event 3272 | Syngenta Seeds, Inc. | Maize line expressing a heat stable alpha-amylase gene amy797E for use in the dry-grind ethanol process. The phosphomannose isomerase gene from *E. coli* was used as a selectable marker. |
| A-153 | Event 98140 | Pioneer Hi-Bred International Inc. | Maize event expressing tolerance to glyphosate herbicide, via expression of a modified bacterial glyphosate N-acetyltransferase, and ALS-inhibiting herbicides, vial expression of a modified form of the maize acetolactate synthase enzyme. |
| A-154 | EXP1910IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). |
| A-155 | FI117 | | Glyphosate resistance |
| A-156 | GA21 | Monsanto Company | Glyphosate resistance: Introduction, by particle bombardment, of a modified 5-enolpyruvyl shikimate-3-phosphate synthase (EPSPS), an enzyme involved in the shikimate biochemical pathway for the production of the aromatic amino acids; |
| A-157 | GA21 × MON810 | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ81Ø-6). |
| A-158 | GAT-ZM1 | | Glufosinate tolerance |
| A-159 | GG25 | | Glyphosate resistance |
| A-160 | GJ11 | | Glyphosate resistance; U.S. Pat. No. 6,040,497 |
| A-161 | IT | Pioneer Hi-Bred International Inc. | Tolerance to the imidazolinone herbicide, imazethapyr, was obtained by in vitro selection of somaclonal variants. |
| A-162 | LY038 | Monsanto Company | Altered amino acid composition, specifically elevated levels of lysine, through the introduction of the cordapA gene, derived from *Corynebacterium glutamicum*, encoding the enzyme dihydrodipicolinate synthase (cDHDPS); |
| A-163 | MIR162 | | Insect resistance |
| A-164 | MIR604 | Syngenta Seeds, Inc. | Corn rootworm resistant maize produced by transformation with a modified cry3A gene. The phosphomannose isomerase gene from *E. coli* was used as a selectable marker; (Cry3a055) |
| A-165 | MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from *Bacillus thuringiensis*. Tolerance to glyphosate herbcicide is derived from GA21. |
| A-166 | MON80100 | Monsanto Company | Insect-resistant maize produced by inserting the cry1Ab gene from *Bacillus thuringiensis* subsp. *kurstaki*. The genetic modification affords resistance to attack by the European corn borer (ECB). |

TABLE A-continued

| | | | |
|---|---|---|---|
| A-167 | MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. |
| A-168 | MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). |
| A-169 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB); |
| A-170 | MON810 × MON88017 | Monsanto Company | Stacked insect resistant and glyphosate tolerant maize derived from conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. |
| A-171 | MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. |
| A-172 | MON863 | Monsanto Company | Corn root worm resistant maize produced by inserting the cry3Bb1 gene from *Bacillus thuringiensis* subsp. *kumamotoensis*. |
| A-173 | MON863 × MON810 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) |
| A-174 | MON863 × MON810 × NK603 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). |
| A-175 | MON863 × NK603 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). |
| A-176 | MON87460 | | Drought tolerance; Water deficit tolerance; |
| A-177 | MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4 (Glyphosate tolerance); |
| A-178 | MON89034 | Monsanto Company | Maize event expressing two different insecticidal proteins from *Bacillus thuringiensis* providing resistance to number of lepidopteran pests; nsect resistance (Lepidoptera-Cry1A.105-Cry2Ab); |
| A-179 | MON89034 × MON88017 | Monsanto Company | Stacked insect resistant and glyphosate tolerant maize derived from conventional cross-breeding of the parental lines MON89034 (OECD identifier: MON-89Ø34-3) and MON88017 (OECD identifier: MON-88Ø17-3). Resistance to Lepiopteran insects is derived from two crygenes present in MON89043. Corn rootworm resistance is derived from a single cry genes and glyphosate tolerance is derived from the 5-enolpyruvylshikimate-3-phosphate synthase (EPSPS) encoding gene from *Agrobacterium tumefaciens* present in MON88017. |

TABLE A-continued

| | | | |
|---|---|---|---|
| A-180 | MON89034 × NK603 | Monsanto Company | Stacked insect resistant and herbicide tolerant maize produced by conventional cross breeding of parental lines MON89034 (OECD identifier: MON-89Ø34-3) with NK603 (OECD unique identifier: MON-ØØ6Ø3-6). Resistance to Lepiopteran insects is derived from two crygenes present in MON89043. Tolerance to glyphosate herbcicide is derived from NK603. |
| A-181 | MON89034 × TC1507 × MON88017 × DAS-59122-7 | Monsanto Company | Stacked insect resistant and herbicide tolerant maize produced by conventional cross breeding of parental lines: MON89034, TC1507, MON88017, and DAS-59122. Resistance to the above-ground and below-ground insect pests and tolerance to glyphosate and glufosinate-ammonium containing herbicides. |
| A-182 | MON-ØØ6Ø3-6 × MON-ØØ81Ø-6 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). |
| A-183 | MON-ØØ81Ø-6 × LY038 | Monsanto Company | Stacked insect resistant and enhanced lysine content maize derived from conventional cross-breeding of the parental lines MON810 (OECD identifier: MON-ØØ81Ø-6) and LY038 (OECD identifier: REN-ØØØ38-3). |
| A-184 | MON-ØØ863-5 × MON-ØØ6Ø3-6 | Monsanto Company | Stacked insect resistant and herbicide tolerant corn hybrid derived from conventional cross-breeding of the parental lines MON863 (OECD identifier: MON-ØØ863-5) and NK603 (OECD identifier: MON-ØØ6Ø3-6). |
| A-185 | MON-ØØ863-5 × MON-ØØ81Ø-6 | Monsanto Company | Stacked insect resistant corn hybrid derived from conventional cross-breeding of the parental lines MON863 (OECD identifier: MON-ØØ863-5) and MON810 (OECD identifier: MON-ØØ81Ø-6) |
| A-186 | MON-ØØ863-5 × MON-ØØ81Ø-6 × MON-ØØ6Ø3-6 | Monsanto Company | Stacked insect resistant and herbicide tolerant corn hybrid derived from conventional cross-breeding of the stacked hybrid MON-ØØ863-5 × MON-ØØ81Ø-6 and NK603 (OECD identifier: MON-ØØ6Ø3-6). |
| A-187 | MON-ØØØ21-9 × MON-ØØ81Ø-6 | Monsanto Company | Stacked insect resistant and herbicide tolerant corn hybrid derived from conventional cross-breeding of the parental lines GA21 (OECD identifier: MON-ØØØ21-9) and MON810 (OECD identifier: MON-ØØ81Ø-6). |
| A-188 | MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). |
| A-189 | MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). |
| A-190 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. |
| A-191 | NK603 × MON810 | Monsanto Company | Stacked insect resistant and herbicide tolerant corn hybrid derived from conventional cross-breeding of the parental lines NK603 (OECD identifier: MON-ØØ6Ø3-6) and MON810 (OECD identifier: MON-ØØ81Ø-6). |
| A-192 | NK603 × T25 | Monsanto Company | Stacked glufosinate ammonium and glyphosate herbicide tolerant maize hybrid derived from conventional cross-breeding of the parental lines NK603 (OECD identifier: MON-ØØ6Ø3-6) and T25 (OECD identifier: ACS-ZM003-2). |
| A-193 | PV-ZMGT32 (NK603) | | Glyphosate tolerance |
| A-194 | E6611.32.1.38/ DP-32138-1/ 32138 | Pioneer Hi-Bred International Inc. | 1) M545: anther-specific 5126 (*Zea mays*) promoter > fertility restoration Ms45 (*Zea mays*) coding sequence > fertility restoration Ms45 (*Zea mays*) 3'-untranslated region 2) ZM-AA1: polygalacturonase 47 (*Zea mays*) promoter > brittle-1 (*Zea mays*) chloroplast transit peptide > alpha-amylase-1 (*Zea mays*) truncated coding sequence > >In2-1 (*Zea mays*) 3'-untranslated region 3) DSRED2: 35S (Cauliflower Mosaic Virus) enhancer > lipid transfer protein-2 (*Hordeum vulgare*) promoter > red fluorescent |

TABLE A-continued

| | | | |
|---|---|---|---|
| A-195 | PV-ZMIR13 (MON863) | | protein (*Dicosoma* sp.) variant coding sequence > protein inhibitor II (*Solanum tuberosum*) 3'-untranslated region Insect resistance (Cry3Bb); |
| A-196 | SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). |
| A-197 | T14 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. |
| A-198 | T14, T25 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. |
| A-199 | T25 × MON810 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). |
| A-200 | TC1507 | Mycogen (c/o Dow AgroSciences); Pioneer (c/o Dupont) | Insect-resistant and glufosinate ammonium herbicide tolerant maize produced by inserting the cry1F gene from *Bacillus thuringiensis* var. *aizawai* and the phosphinothricin N-acetyltransferase encoding gene from *Streptomyces viridochromogenes*; Insect resistance (Cry1F); |
| A-201 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due the presence of the cry1F gene from *Bacillus thuringiensis* var. *aizawai*. Corn rootworm-resistance is derived from DAS-59122-7 which contains the cry34Ab1 and cry35Ab1 genes from *Bacillus thuringiensis* strain PS149B1. Tolerance to glufosinate ammonium herbcicide is derived from TC1507 from the phosphinothricin N-acetyltransferase encoding gene from *Streptomyces viridochromogenes*. |
| A-202 | VIP1034 | | Insect resistance; |
| A-203 | MS-B2 | | Male sterility |
| A-204 | MS-BN1/RF-BN1 | | Male sterility/restoration |
| A-205 | RT73 | | Glyphosate resistance |
| A-206 | MON 87708 | MONSANTO TECHNOLOGY LLC | Dicamba herbicide tolerance, transformation vector PV-GMHT4355 1) DMO: full length transcript (Peanut Chlorotic Streak Virus) promoter > tobacco Etch Virus leader > ribulose 1,5-biphosphate carboxylase small subunit (*Pisum sativum*) chloroplast transit peptide > dicamba mono-oxygenase (*Stenotrophomonas maltophilia*) coding sequence > ribulose-1,5-bisphosphate carboxylase small subunit E9 (*Pisum sativum*) 3'-untranslated region. A CP4 epsps chimeric gene contained within a second T-DNA on the transformation vector used was segregated away. |
| A-207 | EE-GM3/FG72 | BAYER BIOSCIENCE NV [BE]; MS TECHNOLOGIES LLC [US] | 1) Ph4a748 ABBC: sequence including the promoter region of the histone H4 gene of *Arabidopsis thaliana*, containing an internal duplication > 5'tev: sequence including the leader sequence of the tobacco etch virus > TPotp Y: coding sequence of an optimized transit peptide derivative (position 55 changed into Tyrosine), containing sequence of the RuBisCO small subunit genes of *Zea mays* (corn) and *Helianthus annuus* (sunflower) > hppdPf W336: the coding sequence of the 4-hydroxyphenylpyruvate dioxygenase of *Pseudomonas fluorescens* strain A32 modified by the replacement of the amino acid Glycine 336 with a Tryptophane > 3'nos: sequence including the 3' untranslated region of |

| | | | |
|---|---|---|---|
| | | | the nopaline synthase gene from the T-DNA of pTiT37 of *Agrobacterium tumefaciens*. 2) Ph4a748: sequence including the promoter region of the histone H4 gene of *Arabidopsis thaliana* > intron1 h3At: first intron of gene II of the histone H3.III variant of *Arabidopsis thaliana* > TPotp C: coding sequence of the optimized transit peptide, containing sequence of the RuBisCO small subunit genes of *Zea mays* (corn) and *Helianthus annuus* (sunflower) > 2mepsps: the coding sequence of the double-mutant 5-enol-pyruvylshikimate-3-phosphate synthase gene of *Zea mays* > 3'histonAt: sequence including the 3' untranslated region of the histone H4 gene of *Arabidopsis thaliana* |
| A-208 | 416/pDAB4468-0416 | DOW AGROSCIENCES LLC | A novel aad-12 transformation event for herbicide tolerance in soybean plants - referred to herein as pDAB4468-0416. The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants was first disclosed in WO 2007/053482. |
| A-209 | 127 | | ALS/AHAS inhibitor-tolerance |
| A-210 | A5547-35 | | Glufosinate tolerance |
| A-211 | A2704-12 | | Glufosinate tolerance |
| A-212 | Kefeng No. 6 | CHINA NAT RICE RES INST | Transgenic rice Kefeng 6 is a transformation event containing two insect-resistant genes, cry1Ac and SCK (modified CpTI gene) in China. |
| A-213 | 17053 | | Glyphosate tolerance |
| A-214 | 17314 | | Glyphosate tolerance |
| A-215 | Event 1 | | *Fusarium* resistance (trichothecene 3-O-acetyltransferase) |
| A-216 | JOPLIN1 | | disease (fungal) resistance (trichothecene 3-O-acetyltransferase) |
| A-217 | DAS-40278-9 | DOW AgroSciences LLC | RB7 MARv3 > zmUbiquitin 1 promoter > aad1 > zmPER5 3'UTR > RB 7 MARv4. The aad-1 gene confers tolerance to 2,4-dichlorophenoxyacetic acid and aryloxyphenoxypropionate (commonly referred to as "fop" herbicides such as quizalofop) herbicides |
| A-218 | MIR604 | Syngenta Participations AG | 1) CRY3A: metallotionin-like gene (*Zea mays*) promoter > delta-endotoxin cry3a (*Bacillus thuringiensis* subsp. *tenebrionis*) coding sequence, modified to include a cathepsin-G protease recognition site and maize codon optimized > nopaline synthase (*Agrobacterium tumefaciens*) 3'-untranslated region 2) PMI: polyubiquitin (*Zea mays*) promoter (incl. first intron) > mannose-6-phosphate isomerase (*Escherichia coli*) coding sequence > nopaline synthase (*Agrobacterium tumefaciens*) 3'-untranslated region |
| A-219 | MON 87427 | MONSANTO TECHNOLOGY LLC | The transgene insert and expression cassette of MON 87427 comprises the promoter and leader from the cauliflower mosaic virus (CaMV) 35 S containing a duplicated enhancer region (P-e35S); operably linked to a DNA leader derived from the first intron from the maize heat shock protein 70 gene (I-HSP70); operably linked to a DNA molecule encoding an N-terminal chloroplast transit peptide from the shkG gene from *Arabidopsis thaliana* EPSPS (Ts-CTP2); operably linked to a DNA molecule derived from the aroA gene from the *Agrobacterium* sp. strain CP4 and encoding the CP4 EPSPS protein; operably linked to a 3' UTR DNA molecule derived from the nopaline synthase (T-NOS) gene from *Agrobacterium tumefaciens*. |
| A-220 | DP-004114-3 | Pioneer Hi-Bred International Inc. | cry1F, cry34Ab1, cry35Ab1, and pat: resistance to certain lepidopteran and coleopteran pests, as well as tolerance to phosphinothricin. |

TABLE A-continued

| | | | |
|---|---|---|---|
| A-221 | DP-032316-8 | Pioneer Hi-Bred International Inc. | Cry1F, cry34Ab1, cry35Ab1, pat: resistance to certain lepidopteran and coleopteran pests, as well as tolerance to phosphinothricin |
| A-222 | DP-040416-8 a | Pioneer Hi-Bred International Inc. | Cry1F, cry34Ab1, cry35Ab1, pat: resistance to certain lepidopteran and coleopteran pests, as well as tolerance to phosphinothricin |
| A-223 | DP-043A47-3 | Pioneer Hi-Bred International Inc. | Cry1F, cry34Ab1, cry35Ab1, pat: resistance to certain lepidopteran and coleopteran pests, as well as tolerance to phosphinothricin |
| A-224 | 5307 | | Insect (corn rootworm) resistance (FR8a) |

| | Crop | Patent Ref |
|---|---|---|
| A-1 | *Agrostis stolonifera* Creeping Bentgrass | US 2006-162007 |
| A-2 | *Beta vulgaris* (sugar beet) | WO 2010076212 |
| A-3 | *Beta vulgaris* (sugar beet) | WO 2004-074492 |
| A-4 | *Beta vulgaris* (sugar beet) | |
| A-5 | *Beta vulgaris* (sugar beet) | |
| A-6 | *Beta vulgaris* (sugar beet) | US 2004-117870 |
| A-7 | *Brassica napus* (Argentine Canola) | |
| A-8 | *Brassica napus* (Argentine Canola) | |
| A-9 | *Brassica napus* (Argentine Canola) | |
| A-10 | *Brassica napus* (Argentine Canola) | |
| A-11 | *Brassica napus* (Argentine Canola) | |
| A-12 | *Brassica napus* (Argentine Canola) | |
| A-13 | *Brassica napus* (Argentine Canola) | |
| A-14 | *Brassica napus* (Argentine Canola) | |
| A-15 | *Brassica napus* (Argentine Canola) | |
| A-16 | *Brassica napus* (Argentine Canola) | |
| A-17 | *Brassica napus* (Argentine Canola) | |
| A-18 | *Brassica napus* (Argentine Canola) | |
| A-19 | *Brassica napus* (Argentine Canola) | |
| A-20 | *Brassica napus* (Argentine Canola) | |
| A-21 | *Brassica napus* (Argentine Canola) | |
| A-22 | *Brassica napus* (Argentine Canola) | |
| A-23 | *Brassica napus* (Argentine Canola) | WO 02/36831 |
| A-24 | *Brassica napus* (Argentine Canola) | |
| A-25 | *Brassica rapa* (Polish Canola) | |
| A-26 | *Brassica rapa* (Polish Canola) | |
| A-27 | Brinjal | WO 2007/091277 |
| A-28 | *Carica papaya* (Papaya) | |
| A-29 | *Carica papaya* (Papaya) | |
| A-30 | *Cichorium intybus* (Chicory) | |
| A-32 | *Cucumis melo* (Melon) | |
| A-33 | *Cucurbita pepo* (Squash) | |
| A-34 | *Cucurbita pepo* (Squash) | |
| A-35 | *Dianthus caryophyllus* (Carnation) | |
| A-36 | *Dianthus caryophyllus* (Carnation) | |

TABLE A-continued

| | | |
|---|---|---|
| A-37 | *Dianthus caryophyllus* (Carnation) | |
| A-38 | *Glycine max* L. (Soybean) | WO 2008002872, US 2010184079 |
| A-39 | *Glycine max* L. (Soybean) | WO 2006/108674 |
| A-40 | *Glycine max* L. (Soybean) | |
| A-41 | *Glycine max* L. (Soybean) | WO 2006/108675 |
| A-42 | *Glycine max* L. (Soybean) | WO 2008/054747 |
| A-43 | *Glycine max* L. (Soybean) | |
| A-44 | *Glycine max* L. (Soybean) | |
| A-45 | *Glycine max* L. (Soybean) | |
| A-46 | *Glycine max* L. (Soybean) | |
| A-47 | *Glycine max* L. (Soybean) | WO 2009064652 |
| A-48 | *Glycine max* L. (Soybean) | WO 2010037016 |
| A-49 | *Glycine max* L. (Soybean) | WO 2010024976 |
| A-50 | *Glycine max* L. (Soybean) | WO 2009102873 |
| A-51 | *Glycine max* L. (Soybean) | WO2006130436 |
| A-52 | *Glycine max* L. (Soybean) | |
| A-53 | *Glycine max* L. (Soybean) | |
| A-54 | *Glycine max* L. (Soybean) | |
| A-55 | *Gossypium hirsutum* L. (Cotton) | |
| A-56 | *Gossypium hirsutum* L. (Cotton) | WO 2006/128569 |
| A-57 | *Gossypium hirsutum* L. (Cotton) | WO 2006/128570 |
| A-58 | *Gossypium hirsutum* L. (Cotton) | |
| A-59 | *Gossypium hirsutum* L. (Cotton) | |
| A-60 | *Gossypium hirsutum* L. (Cotton) | |
| A-61 | *Gossypium hirsutum* L. (Cotton) | |
| A-62 | *Gossypium hirsutum* L. (Cotton) | |
| A-63 | *Gossypium hirsutum* L. (Cotton) | WO 2006/128573, US 2011020828 |
| A-64 | *Gossypium hirsutum* L. (Cotton) | WO 2006/128571 |
| A-65 | *Gossypium hirsutum* L. (Cotton) | WO 2006/128572 |
| A-66 | *Gossypium hirsutum* L. (Cotton) | US 2006-130175, WO 2004039986, US 2010298553 |
| A-67 | *Gossypium hirsutum* L. (Cotton) | US2009181399 |
| A-68 | *Gossypium hirsutum* L. (Cotton) | US 2007-067868 |
| A-69 | *Gossypium hirsutum* L. (Cotton) | |
| A-70 | *Gossypium hirsutum* L. (Cotton) | |
| A-71 | *Gossypium hirsutum* L. (Cotton) | |
| A-72 | *Gossypium hirsutum* L. (Cotton) | |
| A-73 | *Gossypium hirsutum* L. (Cotton) | WO 2007/017186 |
| A-74 | *Gossypium hirsutum* L. (Cotton) | WO 2008/122406 |
| A-75 | *Gossypium hirsutum* L. (Cotton) | WO 2008151780, US 2010218281 |

TABLE A-continued

| | | |
|---|---|---|
| A-76 | *Gossypium hirsutum* L. (Cotton) | WO 2005/103266 |
| A-77 | *Gossypium hirsutum* L. (Cotton) | |
| A-78 | *Gossypium hirsutum* L. (Cotton) | WO 2005/103266 |
| A-79 | *Gossypium hirsutum* L. (Cotton) | |
| A-80 | *Gossypium hirsutum* L. (Cotton) | |
| A-81 | *Gossypium hirsutum* L. (Cotton) | |
| A-82 | *Gossypium hirsutum* L. (Cotton) | US 2004-250317 |
| A-83 | *Gossypium hirsutum* L. (Cotton) | |
| A-84 | *Gossypium hirsutum* L. (Cotton) | |
| A-85 | *Gossypium hirsutum* L. (Cotton) | |
| A-86 | *Gossypium hirsutum* L. (Cotton) | |
| A-87 | *Gossypium hirsutum* L. (Cotton) | WO 2003013224 |
| A-88 | *Gossypium hirsutum* L. (Cotton) | WO 2004/072235 |
| A-89 | *Gossypium hirsutum* L. (Cotton) | |
| A-90 | *Gossypium hirsutum* L. (Cotton) | US 2004-148666 |
| A-91 | *Gossypium hirsutum* L. (Cotton) | WO 2008/122406, US 2010077501 |
| A-92 | *Gossypium hirsutum* L. (Cotton) | WO 2006/128568 |
| A-93 | *Helianthus annuus* (Sunflower) | |
| A-94 | *Lens culinaris* (Lentil) | |
| A-95 | *Linum usitatissimum* L. (Flax, Linseed) | |
| A-96 | *Lycopersicon esculentum* (Tomato) | |
| A-97 | *Lycopersicon esculentum* (Tomato) | |
| A-98 | *Lycopersicon esculentum* (Tomato) | |
| A-99 | *Lycopersicon esculentum* (Tomato) | |
| A-100 | *Lycopersicon esculentum* (Tomato) | |
| A-101 | *Lycopersicon esculentum* (Tomato) | |
| A-102 | *Medicago sativa* (Alfalfa) | |
| A-103 | *Nicotiana tabacum* L. (Tobacco) | |
| A-104 | *Nicotiana tabacum* L. (Tobacco) | |
| A-105 | *Oryza sativa* (Rice) | |
| A-106 | *Oryza sativa* (Rice) | WO 01/83818 |
| A-107 | *Oryza sativa* (Rice) | US 2008-289060 |
| A-108 | *Oryza sativa* (Rice) | |
| A-109 | *Oryza sativa* (Rice) | |
| A-110 | *Oryza sativa* (Rice) | |
| A-111 | *Oryza sativa* (Rice) | WO 2008/114282 |
| A-112 | *Oryza sativa* (Rice) | |
| A-113 | *Oryza sativa* (Rice) | CN1840655 |
| A-114 | *Prunus domestica* (Plum) | |
| A-115 | *Solanum tuberosum* L. (Potato) | |

TABLE A-continued

| | | |
|---|---|---|
| A-116 | *Solanum tuberosum* L. (Potato) | |
| A-117 | *Solanum tuberosum* L. (Potato) | |
| A-118 | *Solanum tuberosum* L. (Potato) | |
| A-119 | *Solanum tuberosum* L. (Potato) | |
| A-120 | *Triticum aestivum* (Wheat) | |
| A-121 | *Triticum aestivum* (Wheat) | |
| A-122 | *Triticum aestivum* (Wheat) | |
| A-123 | *Triticum aestivum* (Wheat) | |
| A-124 | *Triticum aestivum* (Wheat) | |
| A-125 | *Triticum aestivum* (Wheat) | |
| A-126 | *Triticum aestivum* (Wheat) | |
| A-127 | *Triticum aestivum* (Wheat) | |
| A-128 | *Triticum aestivum* (Wheat) | |
| A-129 | *Zea mays* L. (Maize) | |
| A-130 | *Zea mays* L. (Maize) | US 2006-230473, US 2010063265 |
| A-131 | *Zea mays* L. (Maize) | |
| A-132 | *Zea mays* L. (Maize) | |
| A-133 | *Zea mays* L. (Maize) | |
| A-134 | *Zea mays* L. (Maize) | US 2003-126634 |
| A-135 | *Zea mays* L. (Maize) | |
| A-136 | *Zea mays* L. (Maize) | WO 2010148268 |
| A-137 | *Zea mays* L. (Maize) | |
| A-138 | *Zea mays* L. (Maize) | |
| A-139 | *Zea mays* L. (Maize) | |
| A-140 | *Zea mays* L. (Maize) | |
| A-141 | *Zea mays* L. (Maize) | |
| A-142 | *Zea mays* L. (Maize) | |
| A-143 | *Zea mays* L. (Maize) | |
| A-144 | *Zea mays* L. (Maize) | US 2006-070139, US 2011030086 |
| A-145 | *Zea mays* L. (Maize) | |
| A-146 | *Zea mays* L. (Maize) | |
| A-147 | *Zea mays* L. (Maize) | |
| A-148 | *Zea mays* L. (Maize) | |
| A-149 | *Zea mays* L. (Maize) | |
| A-150 | *Zea mays* L. (Maize) | WO 2008/112019, US 2010240059 |
| A-151 | *Zea mays* L. (Maize) | |
| A-152 | *Zea mays* L. (Maize) | |
| A-153 | *Zea mays* L. (Maize) | |
| A-154 | *Zea mays* L. (Maize) | |
| A-155 | *Zea mays* L. (Maize) | U.S. Pat. No. 6,040,497 |

TABLE A-continued

| | | |
|---|---|---|
| A-156 | *Zea mays* L. (Maize) | U.S. Pat. No. 6,040,497 |
| A-157 | *Zea mays* L. (Maize) | |
| A-158 | *Zea mays* L. (Maize) | WO 01/51654 |
| A-159 | *Zea mays* L. (Maize) | U.S. Pat. No. 6,040,497 |
| A-160 | *Zea mays* L. (Maize) | |
| A-161 | *Zea mays* L. (Maize) | |
| A-162 | *Zea mays* L. (Maize) | U.S. Pat. No. 7,157,281, US 2010212051; US 2007028322 |
| A-163 | *Zea mays* L. (Maize) | WO 2007142840 |
| A-164 | *Zea mays* L. (Maize) | EP 1 737 290 |
| A-165 | *Zea mays* L. (Maize) | |
| A-166 | *Zea mays* L. (Maize) | |
| A-167 | *Zea mays* L. (Maize) | |
| A-168 | *Zea mays* L. (Maize) | |
| A-169 | *Zea mays* L. (Maize) | US 2004-180373 |
| A-170 | *Zea mays* L. (Maize) | |
| A-171 | *Zea mays* L. (Maize) | |
| A-172 | *Zea mays* L. (Maize) | |
| A-173 | *Zea mays* L. (Maize) | |
| A-174 | *Zea mays* L. (Maize) | |
| A-175 | *Zea mays* L. (Maize) | |
| A-176 | *Zea mays* L. (Maize) | WO 2009/111263 |
| A-177 | *Zea mays* L. (Maize) | WO2005059103 |
| A-178 | *Zea mays* L. (Maize) | WO 2007140256 |
| A-179 | *Zea mays* L. (Maize) | |
| A-180 | *Zea mays* L. (Maize) | |
| A-181 | *Zea mays* L. (Maize) | |
| A-182 | *Zea mays* L. (Maize) | |
| A-183 | *Zea mays* L. (Maize) | |
| A-184 | *Zea mays* L. (Maize) | |
| A-185 | *Zea mays* L. (Maize) | |
| A-186 | *Zea mays* L. (Maize) | |
| A-187 | *Zea mays* L. (Maize) | |
| A-188 | *Zea mays* L. (Maize) | |
| A-189 | *Zea mays* L. (Maize) | |
| A-190 | *Zea mays* L. (Maize) | |
| A-191 | *Zea mays* L. (Maize) | |
| A-192 | *Zea mays* L. (Maize) | |
| A-193 | *Zea mays* L. (Maize) | US 2007-056056 |
| A-194 | zea mays L. (Maize) | WO 2009103049, MX 2010008977 |

TABLE A-continued

| | | | |
|---|---|---|---|
| A-195 | | Zea mays L. (Maize) | US 2006-095986 |
| A-196 | | Zea mays L. (Maize) | |
| A-197 | | Zea mays L. (Maize) | |
| A-198 | | Zea mays L. (Maize) | |
| A-199 | | Zea mays L. (Maize) | |
| A-200 | | Zea mays L. (Maize) | U.S. Pat. No. 7,435,807 |
| A-201 | | Zea mays L. (Maize) | |
| A-202 | | Zea mays L. (Maize) | WO 03/052073 |
| A-203 | | Brassica ssp | WO 01/31042 |
| A-204 | | Brassica ssp | WO 01/41558 |
| A-205 | | Brassica ssp | WO 02/36831 |
| A-206 | | Glycine max L. (Soybean) | WO 2011034704 |
| A-207 | | Glycine max L. (Soybean) | WO 2011063411 |
| A-208 | | Glycine max L. (Soybean) | WO 2011066384 |
| A-209 | | Glycine max L. (Soybean) | WO 2010080829 |
| A-210 | | Glycine max L. (Soybean) | WO 2006/108675 |
| A-211 | | Glycine max L. (Soybean) | WO 2006/108674 |
| A-212 | | Oryza sativa (Rice) | CN 101824411 |
| A-213 | | Oryza sativa (Rice) | WO 2010117737 |
| A-214 | | Oryza sativa (Rice) | WO 2010117735 |
| A-215 | | Wheat | CA 2561992 |
| A-216 | | Wheat | US 2008064032 |
| A-217 | | Zea mays L. (Maize) | WO 2011022469 |
| A-218 | | Zea mays L. (Maize) | US 2005216970, US 2008167456, US 2011111420 |
| A-219 | | Zea mays L. (Maize) | WO 2011062904 |
| A-220 | | Zea mays L. (Maize) | US 2011154523 |
| A-221 | | Zea mays L. (Maize) | US 2011154524 |
| A-222 | | Zea mays L. (Maize) | US 20110154525 |
| A-223 | | Zea mays L. (Maize) | US20110154526 |
| A-224 | | Zea mays L. (Maize) | WO2010077816 |

Formulations

Suitable extenders and/or surfactants which may be contained in the compositions according to the invention are all formulation auxiliaries which can customarily be used in plant treatment compositions.

When employing the active compounds of the formula (I) which can be used according to the invention, the application rates can be varied within a certain range, depending on the type of application.

According to the invention, carrier is to be understood as meaning a natural or synthetic, organic or inorganic substance which is mixed or combined with the active compounds for better applicability, in particular for application to plants or plant parts. The carrier, which may be solid or liquid, is generally inert and should be suitable for use in agriculture.

Suitable solid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, and also protein hydrolysates. Suitable dispersants are: for example lignosulphite waste liquors and methylcellulose.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight of the active compound combination according to the invention, preferably between 10 and 70 percent by weight, particularly preferably between 20 and 50 percent by weight, most preferably 25 percent by weight.

Compounds of formula (I) be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, suspension concentrates, suspoemulsion concentrates, soluble concentrates, suspensions, wettable powders, soluble powders, dusts and granules, water-soluble granules or tablets, wettable powders, natural products and synthetic substances impregnated with active compound, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

Organic diluents that may be present are all polar and non-polar organic solvents that are customarily used for such purposes. Preferred are ketones, such as methyl isobutyl ketone and cyclohexanone, furthermore amides, such as dimethylformamide and alkanecarboxamides, such as N,N-dimethyldecan-amide and N,N-dimethyloctanamide, furthermore cyclic compounds, such as N-methylpyrrolidone, N-octylpyrrolidone, N-dodecylpyrrolidone, N-octylcaprolactam, N-dodecylcaprolactam and butyrolactone, additionally strongly polar solvents, such as dimethyl sulphoxide, furthermore aromatic hydrocarbons, such as xylene, Solvesso™, mineral oils, such as white spirit, petroleum, alkylbenzenes and spindle oil, moreover esters, such as propylene glycol monomethyl ether acetate, dibutyl adipate, hexyl acetate, heptyl acetate, tri-n-butyl citrate and di-n-butyl phthalate, and furthermore alcohols, such as, for example, benzyl alcohol and 1-methoxy-2-propanol.

Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable surfactants (adjuvants, emulsifiers, dispersants, protective colloids, wetting agents and tackifiers) are customary ionic and nonionic substances. Examples which may be mentioned are ethoxylated nonylphenols, polyalkylene glycol ethers of straight-chain or branched alcohols, products of reactions of alkylphenols with ethylene oxide and/or propylene oxide, products of reactions of fatty amines with ethylene oxide and/or propylene oxide, furthermore fatty esters, alkylsulphonates, alkyl sulphates, alkyl ether sulphates, alkyl ether phosphates, aryl sulphates, ethoxylated arylalkylphenols, such as, for example, tristyrylphenol ethoxylates, furthermore ethoxylated and propoxylated arylalkylphenols and also sulphated or phosphated arylalkylphenol ethoxylates or ethoxy- and propoxylates. Mention may furthermore be made of natural and synthetic water-soluble polymers, such as lignosulphonates, gelatine, gum arabic, phospholipids, starch, hydrophobically modified starch and cellulose derivatives, in particular cellulose esters and cellulose ethers, furthermore polyvinyl alcohol, polyvinyl acetate, polyvinylpyrrolidone, polyacrylic acid, polymethacrylic acid and copolymers of (meth)acrylic acid and (meth)acrylic acid esters, and moreover also alkali metal hydroxide-neutralized copolymers of methacrylic acid and methacrylic ester and condensates of optionally substituted naphthalenesulphonic acid salts with formaldehyde.

Suitable solid fillers and carriers are all substances customarily used for this purpose in crop pretection compositions. Inorganic particles, such as carbonates, silicates, sulphates and oxides having a mean particle size of from 0.005 to 20 µm, particularly preferably from 0.02 to 10 µm, may be mentioned as being preferred. Examples which may be mentioned are ammonium sulphate, ammonium phosphate, urea, calcium carbonate, calcium sulphate, magnesium sulphate, magnesium oxide, aluminium oxide, silicon dioxide, finely divided silicic acid, silica gels, natural and synthetic silicates and alumosilicates and vegetable products such as cereal meal, wood powder and cellulose powder.

The formulations generally comprise between 0.1 and 95% by weight of active compound, preferably between 0.5 and 90%.

The active compound combinations according to the invention can be present in commercial formulations and in the use forms prepared from these formulations as a mixture with other active compounds, such as insecticides, attractants, sterilants, bactericides, acaricides, nematicides, fungicides, growth regulators or herbicides. A mixture with fertilizers is also possible.

The treatment according to the invention of the plants and plant parts with the active compound combinations or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material. Preference is given to application by dipping, spraying, atomizing, irrigating, evaporating, dusting, fogging, broadcasting, foaming, painting, spreading-on, watering (drenching) and drip irrigating.

The application of the formulations is carried out in accordance with customary agricultural practice in a manner adapted to the application forms. Customary applications are, for example, dilution with water and spraying of the resulting spray liquor, application after dilution with oil, direct application without dilution, or soil application of carrier granules.

The active compound content of the application forms prepared from the commercial formulations can vary within wide limits. The active compound concentration of the application forms can be from 0.0000001 up to 95% by weight of active compound, preferably between 0.0001 and 2% by weight.

The compositions according to the invention do not only comprise ready-to-use compositions which can be applied with suitable apparatus to the plant, but also commercial concentrates which have to be diluted with water prior to use.

Application Methods

The treatment according to the invention of the plants and plant parts with compounds of formula (I) is carried out directly or by action on their surroundings, habitat or storage space using customary treatment methods, for example by dipping, spraying, atomizing, irrigating, stem injection, in-furrow application, evaporating, dusting, fogging, broadcasting, foaming, painting, spreading-on, watering (drenching), drip irrigating. It is furthermore possible to apply the active compounds by the ultra-low volume method, or to inject the active compound preparation or the active compound itself into the soil.

The control of nematodes which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

The nematicidal compositions according to the invention can be used for the curative or protective control of nematodes. Accordingly, the invention also relates to curative and protective methods for controlling nematodes using compounds of formula (I), which are applied to the plant or plant parts, the fruit or the soil in which the plants grow. Preference is given to application onto the plant or the plant parts, the fruits or the soil.

The compositions according to the invention for controlling nematodes in crop protection comprise an active, but non-phytotoxic amount of the compounds according to the invention. "Active, but non-phytotoxic amount" shall mean an amount of the composition according to the invention which is sufficient to control or to completely kill the plant disease caused by nematodes, which amount at the same time does not exhibit noteworthy symptoms of phytotoxicity. These application rates generally may be varied in a broader range, which rate depends on several factors, e.g. the nematodes, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and of the soil.

In a further embodiment the present invention relates to the use of compounds of formula (I) for controlling *Meloidogyne incognita* in tomato.

In a further embodiment the present invention relates to the use of compounds of formula (I) for controlling *Helicotylenchus* sp. in tomato.

In a further embodiment the present invention relates to the use of compounds of formula (I) for controlling *Meloidogyne hapla* in potato.

In a further embodiment the present invention relates to the use of compounds of formula (I) for controlling *Tylenchulus semipenetrans* in citrus.

In a further embodiment the present invention relates to the use of compounds of formula (I) for controlling *Radopholus similis* in banana.

In a further embodiment the present invention relates to a method of treatment comprising applying compounds of formula (I) as a plant drench application for controlling nematodes.

In a further embodiment the present invention relates to a method of treatment comprising applying compounds of formula (I) as a plant drench application for controlling nematodes in tomato.

In a further embodiment the present invention relates to a method of treatment comprising applying compounds of formula (I) as a plant in-furrow application for controlling nematodes.

In a further embodiment the present invention relates to a method of treatment comprising applying compounds of formula (I) as a plant in-furrow application for controlling nematodes in potato.

In a further embodiment the present invention relates to a method of treatment comprising applying compounds of formula (I) as a drench application for controlling nematodes.

In a further embodiment the present invention relates to a method of treatment comprising applying compounds of formula (I) as a drench application for controlling nematodes in citrus.

In a further embodiment the present invention relates to a method of treatment comprising applying compounds of formula (I) as a drench application for controlling nematodes in banana.

In a further embodiment the present invention relates to a method of treatment comprising applying compounds of formula (I) as a stem injection application for controlling nematodes.

In a further embodiment the present invention relates to a method of treatment comprising applying compounds of formula (I) as a stem injection application for controlling nematodes in banana.

In a further embodiment the present invention relates to the use of compositions comprising compounds of formula (I) for controlling *Meloidogyne incognita* in tomato.

In a further embodiment the present invention relates to the use of compositions comprising compounds of formula (I) for controlling *Helicotylenchus* sp. in tomato.

In a further embodiment the present invention relates to the use of compositions comprising compounds of formula (I) for controlling *Meloidogyne hapla* in potato.

In a further embodiment the present invention relates to the use of compositions comprising compounds of formula (I) for controlling *Tylenchulus semipenetrans* in citrus.

In a further embodiment the present invention relates to the use of compositions comprising compounds of formula (I) for controlling *Radopholus similis* in banana.

In a further embodiment the present invention relates to a method of treatment comprising applying compositions comprising compounds of formula (I) as a plant drench application for controlling nematodes.

In a further embodiment the present invention relates to a method of treatment comprising applying compositions comprising compounds of formula (I) as a plant drench application for controlling nematodes in tomato.

In a further embodiment the present invention relates to a method of treatment comprising applying compositions comprising compounds of formula (I) as a plant in-furrow application for controlling nematodes.

In a further embodiment the present invention relates to a method of treatment comprising applying compositions comprising compounds of formula (I) as a plant in-furrow application for controlling nematodes in potato.

In a further embodiment the present invention relates to a method of treatment comprising applying compositions comprising compounds of formula (I) as a drench application for controlling nematodes.

In a further embodiment the present invention relates to a method of treatment comprising applying compositions comprising compounds of formula (I) as a drench application for controlling nematodes in citrus.

In a further embodiment the present invention relates to a method of treatment comprising applying compositions comprising compounds of formula (I) as a drench application for controlling nematodes in banana.

In a further embodiment the present invention relates to a method of treatment comprising applying compositions comprising compounds of formula (I) as a stem injection application for controlling nematodes.

In a further embodiment the present invention relates to a method of treatment comprising applying compositions comprising compounds of formula (I) as a stem injection application for controlling nematodes in banana.

The following synthesis examples illustrate the preparation of the compounds of formula (I).

Synthesis Example A

Preparation of N-[1-(2,6-difluorophenyl)-1H-pyrazol-3-yl]-2-(trifluoromethyl)benzamide (compound (I-1-75))

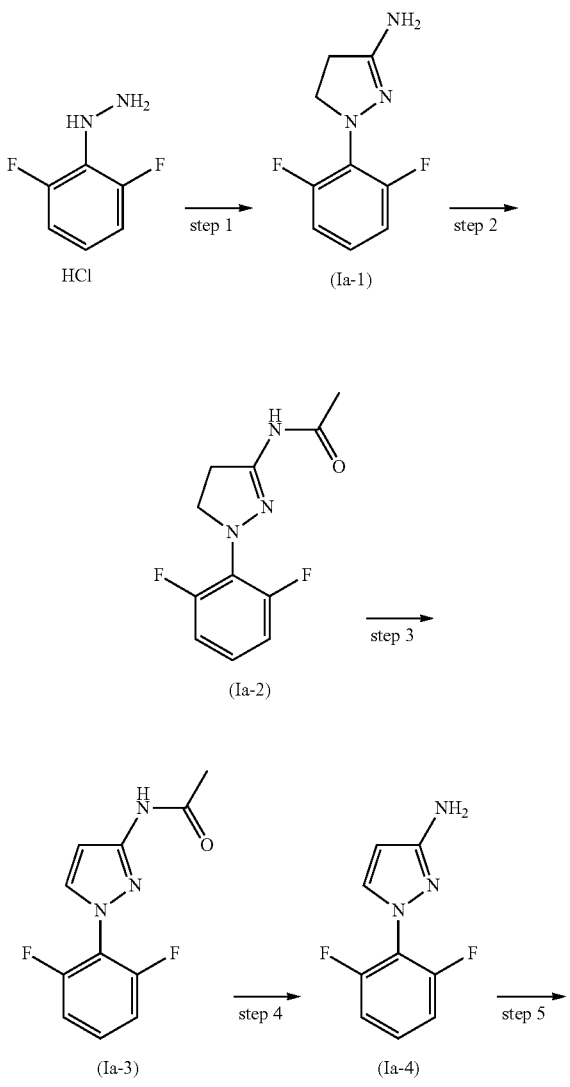

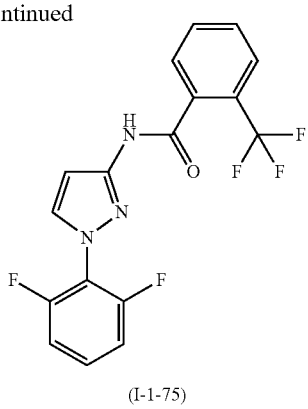

(I-1-75)

Step 1: 1-(2,6-Difluorophenyl)-4,5-dihydro-1H-pyrazole-3-amine (intermediate (Ia-1))

2,6-Difluorophenylhydrazine hydrochloride (2.00 g) was initially charged in ethanol (20 ml), sodium ethoxide (21% in ethanol, 3.02 g) was slowly added dropwise at room temperature, the mixture was stirred for 10 min, acrylonitrile (0.80 ml) was added and the mixture was heated under reflux overnight. The reaction mixture was then concentrated under reduced pressure, taken up in dichloromethane, washed with water, dried over sodium sulphate and concentrated to dryness under reduced pressure. What remained was 1.40 g of the title compound which was used without further purification for the next step.

Step 2: N-[1-(2,6-Difluorophenyl)-4,5-dihydro-1H-pyrazol-3-yl]acetamide (intermediate (Ia-2))

With ice cooling, 1-(2,6-difluorophenyl)-4,5-dihydro-1H-pyrazole-3-amine (Ia-1) (1.40 g from previous step) was dissolved in acetic anhydride (6 ml) and stirred at room temperature overnight. The mixture was then diluted with ethyl acetate, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 537 mg of the title compound. HPLC-MS: log P=1.46; mass (m/z): 240.0 (M+H)+; 1H-NMR (DMSO-D6) 1.99 (s, 3H), 3.26 (t, 2H), 3.65 (t, 2H), 7.04-7.10 (m, 2H), 7.11-7.18 (m, 1H), 10.59 (br. s, 1H).

Step 3: N-[1-(2,6-Difluorophenyl)-1H-pyrazol-3-yl]acetamide (intermediate (Ia-3))

N-[1-(2,6-Difluorophenyl)-4,5-dihydro-1H-pyrazol-3-yl]acetamide (Ia-2) (200 mg) was initially charged in 1,4-dioxane (1 ml), 2,3-dichloro-5,6-dicyano-1,4-benzoquinone (209 mg) was added and the mixture was stirred at room temperature for 30 min. The reaction mixture was filtered and the filtrate was concentrated to dryness under reduced pressure. The residue was purified by column chromatography on silica gel using the mobile phase cyclohexane/ethyl acetate (gradient=2 h from 100% cyclohexane to 100% ethyl acetate). This gave 140 mg of the title compound.
HPLC-MS: log P=1.33; mass (m/z): 238.0 (M+H)+; 1H-NMR (CD3CN) 2.07 (s, 3H), 6.84 (d, 1H), 7.14-7.20 (m, 2H), 7.47-7.53 (m, 1H), 7.65-7.66 (m, 1H), 8.76 (br. s, 1H).

Step 4: 1-(2,6-Difluorophenyl)-1H-pyrazole-3-amine (intermediate (Ia-4))

N-[1-(2,6-Difluorophenyl)-1H-pyrazol-3-yl]acetamide (Ia-3) (50 mg) was initially charged in water (1 ml), concentrated hydrochloric acid (0.07 ml) was added and the mixture was heated under reflux for 8 h. The reaction mixture was then made alkaline with concentrated aqueous sodium hydroxide solution and extracted with dichloromethane. The organic phase was concentrated to dryness under reduced pressure. This gave 25 mg of the title compound.
HPLC-MS: log P=1.13; mass (m/z): 196.1 (M+H)+; 1H-NMR (CD3CN) 4.12 (br. s, 2H), 5.83 (d, 1H), 7.09-7.16 (m, 2H), 7.37-7.44 (m, 1H), 7.46-7.47 (m, 1H).

Step 5: N-[1-(2,6-difluorophenyl)-1H-pyrazol-3-yl]-2-(trifluoromethyl)benzamide (compound (I-1-75))

1-(2,6-Difluorophenyl)-1H-pyrazole-3-amine (Ia-4) (1 g) was initially charged in dichloromethane (10 ml). The reaction mixture was cooled down to 0° C.; 2.142 mL of triethylamine were added. Then 2-(trifluoromethyl)benzoyl chloride (1.175 g) was added dropwise with a temperature between 0° C. and 5° C. The reaction mixture was stirred overnight at room temperature. Some dichloromethane and water were then added. The organic phase was separated, dried and evaporated. The residue obtained was purified by column chromatography on silica gel using a gradient of cyclohexane/ethyl acetate. This gave 1.2 g of the title compound.
HPLC-MS: log P=2.68; mass (m/z): 368.1 (M+H)+; 1H-NMR [CD3CN] 6.99 (d, 1H), 7.16-7.22 (m, 2H), 7.47-7.54 (m, 1H), 7.65-7.76 (m, 4H), 7.80-7.82 (m, 1H), 9.30 (br. s, 1H).

Synthesis Example B

Preparation of N-[1-(3,5-difluoropyridin-2-yl)-1H-pyrazol-3-yl]-2-(trifluoromethyl)benzamide (compound (I-1-140))

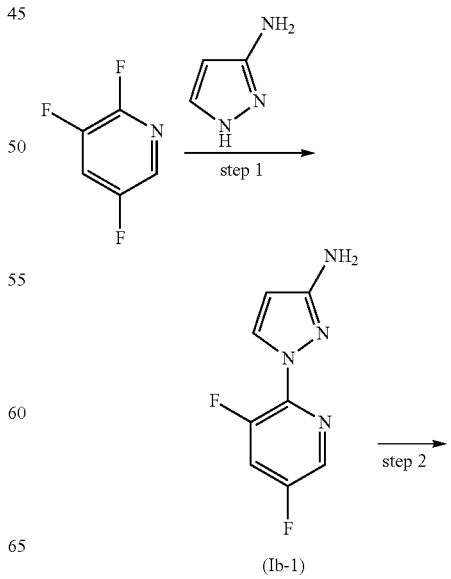

(Ib-1)

69

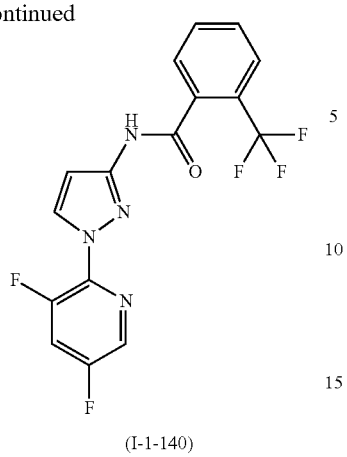

(I-1-140)

Step 1: 1-(3,5-Difluoropyridin-2-yl)-1H-pyrazole-3-amine (intermediate (Ib-1)

1H-Pyrazole-3-amine (1.80 g) was initially charged in acetonitrile (50 ml), 2,3,5-trifluoropyridine (2.88 g) and potassium carbonate (5.99 g) were added and the mixture was heated under reflux overnight. The reaction mixture was then concentrated under reduced pressure, taken up in dichloromethane, washed with water, dried over sodium sulphate and concentrated to dryness under reduced pressure. The residue was purified by column chromatography on silica gel using the mobile phase cyclohexane/ethyl acetate (gradient=2 h from 100% cyclohexane to 100% ethyl acetate). This gave 610 mg of the title compound.

HPLC-MS: log P=0.81; mass (m/z): 197.1 (M+H)+; 1H-NMR (CD3CN) 4.27 (br. s, 2H), 5.88 (d, 1H), 7.56-7.62 (m, 1H), 7.99-8.00 (m, 1H), 8.17-8.18 (m, 1H).

Step 2: N-[1-(3,5-difluoropyridin-2-yl)-1H-pyrazol-3-yl]-2-(trifluoromethyl)benzamide (compound (I-1-140))

1-(3,5-Difluoropyridin-2-yl)-1H-pyrazole-3-amine (Ib-1) (300 mg) was initially charged in dichloromethane (2 ml). The reaction mixture was cooled down to 0° C.; 0.640 ml of triethylamine were added. Then 2-(trifluoromethyl)benzoyl chloride (0.256 ml) was added dropwise with a temperature between 0° C. and 5° C. The reaction mixture was stirred overnight at room temperature. Some dichloromethane and water were then added. The organic phase was separated, dried and evaporated. The residue obtained was purified by column chromatography on silica gel using a gradient of cyclohexane/ethyl acetate. This gave 506 mg of the title compound.

HPLC-MS: log P=2.48; mass (m/z): 369.1 (M+H)+; 1H-NMR [CD3CN] 7.03 (d, 1H), 7.62-7.70 (m, 4H), 7.77-7.79 (m, 1H), 8.20 (d, 1H), 8.25 (d, 1H), 9.47 (br. s, 1H).

70

Synthesis Example C

Preparation of N-[2-(2,6-Difluorophenyl)-2H-1,2,3-triazol-4-yl]-2-(trifluoromethyl)benzamide (compound (I-2-35))

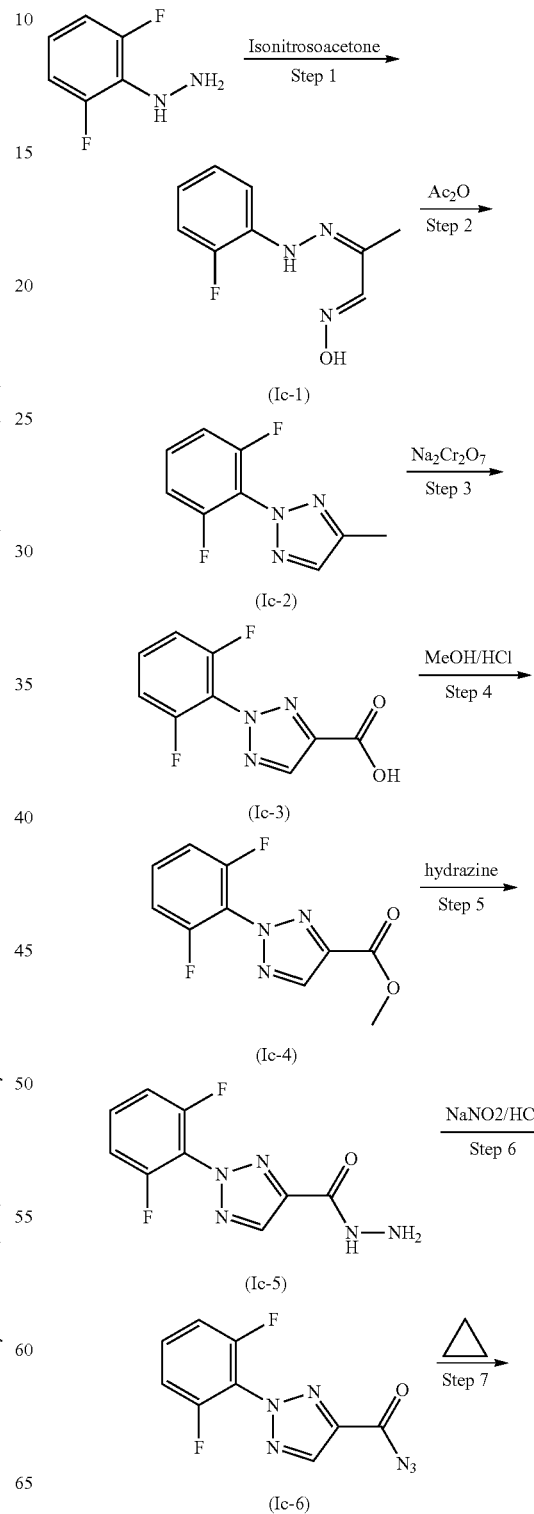

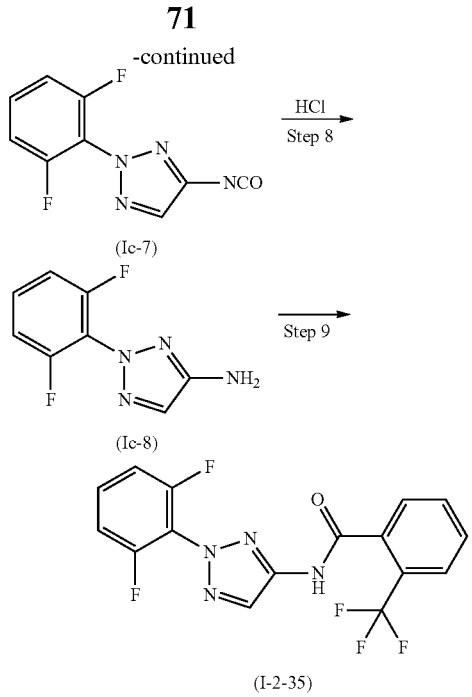

Step 1: 2-[2-(2,6-Difluorophenyl)hydrazinylidene]propanal oxime (intermediate (Ic-1))

0.1 mol of 2,6-difluorophenylhydrazine and 0.12 mol of isonitrosoacetone were heated under reflux in ethanol for 3 h. After cooling to room temperature, the precipitated solid was filtered off, washed with ethanol and dried. This gave the title compound (75% of theory)

Step 2: 2-(2,6-Difluorophenyl)-4-methyl-2H-1,2,3-triazole (intermediate (Ic-2))

A solution of 0.1 mol of the 2-[2-(2,6-difluorophenyl)hydrazinylidene]propanal oxime (Ic-1) in acetic anhydride was heated slowly to 120° C. and stirred at this temperature for 2 h. Excess of acetic anhydride was removed on a rotary evaporator. The title compound was obtained (65% of theory) and was used without further purification.

Step 3: 2-(2,6-Difluorophenyl)-2H-1,2,3-triazole-4-carboxylic acid (intermediate (Ic-3))

0.2 mol of sodium dichromate was added to a well-stirred solution of 0.1 mol of 2-(2,6-difluorophenyl)-4-methyl-2H-1,2,3-triazole (Ic-2) in 66% sulphuric acid. Each individual portion of dichromate was added only after the yellow-orange colour of the Cr6+ in the flask had disappeared. Moreover, the portions were added such that the temperature in the flask remained at about 80-90° C. The mixture was then heated for 1 h. After cooling, the mixture was poured into about the same amount of ice and allowed to stand overnight. The precipitated acid (Ic-3) was filtered off, washed with water and dried. This gave the title compound (50% of theory).

Step 4: Methyl 2-(2,6-difluorophenyl)-2H-1,2,3-triazole-4-carboxylate (intermediate (Ic-4))

Hydrogen chloride was bubbled for 2 h through a boiling solution of 2-(2,6-difluorophenyl)-2H-1,2,3-triazole-4-carboxylic acid (Ic-3) in methanol. After cooling, white crystals of the title compound were filtered off (85% of theory).

Step 5: 2-(2,6-Difluorophenyl)-2H-1,2,3-triazole-4-carbohydrazide (intermediate (Ic-5))

Methyl 2-(2,6-difluorophenyl)-2H-1,2,3-triazole-4-carboxylate (Ic-4) was boiled with an excess of 1.5 eq. of hydrazine hydrate in ethanol for 4 h. After cooling, the crystals of the hydrazide (Ic-5) were boiled with water and dried. This gave the title compound (90% of theory).

Step 6: 2-(2,6-Difluorophenyl)-2H-1,2,3-triazole-4-carbonylazide (intermediate (Ic-6))

An aqueous solution of sodium nitrite was added to a suspension of 2-(2,6-Difluorophenyl)-2H-1,2,3-triazole-4-carbohydrazide (Ic-5) in 20% aqueous hydrochloric acid. After further stirring at 10° C., the crystals of the acyl azide (Ic-6) were filtered off, washed with water and dried at room temperature under reduced pressure. This gave the title compound (75% of theory).

Step 7: 2-(2,6-Difluorophenyl)-2H-1,2,3-triazole-4-carbonyl isocyanate (intermediate (Ic-7))

2-(2,6-Difluorophenyl)-2H-1,2,3-triazole-4-carbonyl azide (Ic-6) dried was boiled in toluene until the evolution of gas had ended (about 2 h). The toluene was then removed on a rotary evaporator and the viscous residue of the isocyanate (Ic-7) was directly ready for the next step without further purification. This gave the title compound (90% of theory).

Step 8: 2-(2,6-Difluorophenyl)-2H-1,2,3-triazole-4-amine (intermediate (Ic-8))

2-(2,6-Difluorophenyl)-2H-1,2,3-triazole-4-carbonyl isocyanate (Ic-7) was hydrolyzed by 30 min of boiling in hydrochloric acid. Residual volatile substances were removed on a rotary evaporator, and the residue was treated with sodium carbonate solution. The precipitated crystals were filtered off, washed with water and recrystallized from hexane. This gave the title compound (70% of theory).

HPLC-MS: log P=1.16; mass (m/z): 197.0 (M+H)+; 1H-NMR (CD3CN) 5.46 (b, 2H), 7.33-7.38 (m, 3H), 7.56-7.64 (m, 1H).

Step 9: N-[2-(2,6-Difluorophenyl)-2H-1,2,3-triazol-4-yl]-2-(trifluoromethyl)benzamide (Compound I-2-35)

2, 2-(2,6-difluorophenyl)-2H-1,2,3-triazole-4-amine (Ic-8) (150 mg) was reacted with 2-(trifluoromethyl)benzoyl chloride (160 mg) and triethylamine (0.21 ml) in 3.9 ml of dichloromethane. Purification by column chromatography and preparative HPLC gave 143 mg of the title compound.

HPLC-MS: log P=2.80; mass (m/z): 369.1 (M+H)+; 1H-NMR (CD3CN) 7.45-7.49 (m, 2H), 7.70-7.77 (m, 4H), 7.78-7.88 (m, 1H), 8.45 (s, 1H), 11.83 (s, 1H).

Synthesis Example D

Preparation of N-[1-(3,5-difluoropyridin-2-yl)-1H-pyrazol-3-yl]-N-ethyl-2-(trifluoromethyl)benzamide (compound (I-1-468))

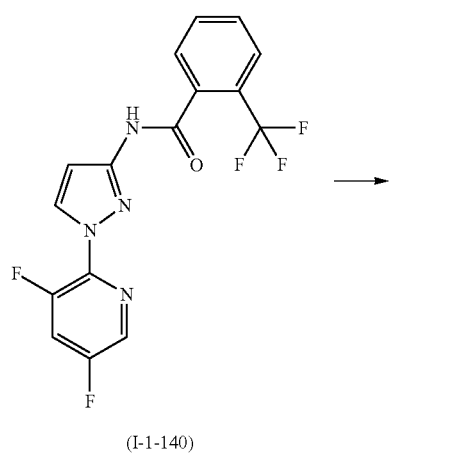

(I-1-140)

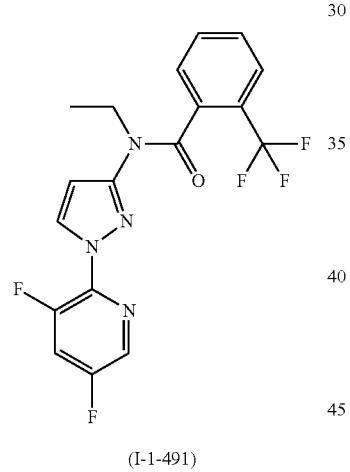

(I-1-491)

N-[1-(3,5-difluoropyridin-2-yl)-1H-pyrazol-3-yl]-2-(trifluoromethyl)benzamide (compound (I-1-140), 1 equiv) was placed in dry THF. NaH (1.5 equiv) was added at 0° C. The reaction mixture was stirred for 30 minutes. Ethyliodide (1.5 equiv) was then added and the reaction mixture was stirred overnight at room temperature. Another 1 equivalent (twice 0.5 equivalents) of NaH and of ethyliodide were added. The reaction mixture was stirred at 50° C. overnight. The reaction mixture was cooled down, quenched with water and extracted with ethylacetate. The gathered organic phases were dried and evaporated. The residue was purified and this gave the title compound. HPLC-MS and 1H-NMR: see table below (Compound I-1-468).

Synthesis Example D-BIS

N-[1-(3-Cyanopyrazin-2-yl)-1H-pyrazol-3-yl]-2-(trifluoromethyl)benzamide (Compound (I-1-574))

Step 1:
N-(1H-Pyrazol-3-yl)-2-(trifluoromethyl)benzamide

With exclusion of moisture, a solution of 3-aminopyrazole (43.9 g) and triethylamine (52.4 g) in acetonitrile (400 ml) was stirred at 0° C. for one hour. A solution of 2-(trifluoromethyl)benzoyl chloride (109.1 g) in acetonitrile (50 ml) was then added dropwise such that the internal temperature did not exceed 7° C. The reaction was allowed to warm to room temperature overnight, diluted with 600 ml of water and extracted with ethyl acetate. The combined organic phases were dried over magnesium sulphate, filtered and concentrated. The residue obtained in this manner was dissolved in isopropanol (500 ml) under reflux. After cooling to room temperature, the crystals that had separated out were isolated (48.6 g). This was the title compound with one molar equivalent of isopropanol of crystallization. HPLC-MS: log P=1.33, mass (m/z): 255.9 (M+H)$^+$; (DMSO-D6) 1.03 (m, 6H), 3.77 (m, 1H), 4.33 (m, 1H), 6.60 (m, 1H), 7.60-7.81 (m, 5H), 10.97 (s, 1H), 12.41 (m, 1H).

Step 2: N-[1-(3-Cyanopyrazin-2-yl)-1H-pyrazol-3-yl]-2-(trifluoromethyl)benzamide (Compound (I-1-574))

The title compound was obtained starting with 3-chloropyrazine-2-carbonitrile and N-(1H-pyrazol-3-yl)-2-(trifluoromethyl)benzamide using potassium carbonate as a base.

HPLC-MS: log P=2.47; mass (m/z): 359.0 (M+H)+;
1H-NMR (DMSO-D6) 7.12 (m, 1H), 7.72 (m, 2H), 7.78 (m, 1H), 7.83 (m, 1H), 8.63 (m, 1H), 8.75 (m, 1H), 8.85 (m, 1H), 11.71 (s, 1H).

Solvents used were CD3CN or DMSO-D6, and tetramethylsilane (0.00 ppm) was used as reference. In individual cases, the NMR spectra were determined using a Bruker Avance II 600. Solvents used were CD3CN or DMSO-D6, and tetramethylsilane (0.00 ppm) was used as reference.

HPLC-MS1) and 1H-NMR data 2)

Compound No.
HPLC-MS1) and 1H-NMR data2)
I-1-75
see synthesis Example A
I-1-83
HPLC-MS: logP = 2.67; mass (m/z): 426.1 (M + H)+; 1H-NMR [CD3CN] 7.01 (d, 1H), 7.16-7.23 (m, 3H), 7.46-7.54 (m, 3H), 7.76 (d, 1H), 7.93-7.95 (m, 1H), 9.15 (br. s, 1H).
I-1-140
see synthesis Example B
I-1-468:
HPLC-MS: logP = 3.23; mass (m/z): 397.1 (M + H)+; 1H-NMR(400.0 MHz, DMSO-D6): δ =
8.501(1.2); 8.415(4.9); 8.410(5.1); 8.383(1.3); 8.317(0.5); 8.291(0.4); 8.270(0.7); 8.244(0.5); 8.219(1.5);
8.213(1.5); 8.192(2.8); 8.171(2.1); 8.166(2.1); 8.151(5.2); 8.145(5.4); 8.078(1.5); 8.073(1.7); 7.895(1.2);
7.870(1.9); 7.864(2.0); 7.832(1.1); 7.819(1.2); 7.794(0.5); 7.767(1.3); 7.741(2.9); 7.717(4.5); 7.702
(3.4); 7.696(3.2); 7.554(2.4); 7.535(6.5); 7.527(6.4); 7.518(5.1); 7.343(3.4); 7.335(3.5); 7.322(2.6);
7.047(1.3);6.933(0.6); 6.060(5.2); 6.054(5.4); 5.757(0.7); 5.722(1.6); 5.717(1.7); 4.206(0.6); 4.189(0.6);
4.128(0.8); 4.111(2.0); 4.094(2.1); 4.077(0.7); 3.937(3.2); 3.833(0.7); 3.480(0.5); 3.322(131.8); 2.675(2.4);
2.671(3.2); 2.667(2.5); 2.506(379.2); 2.502(482.3); 2.497(374.3); 2.333(2.4); 2.328(3.2); 2.324(2.5);
1.352(0.7); 1.336(1.2); 1.319(0.7); 1.260(2.2); 1.243(4.7); 1.227(9.5); 1.210(16.0); 1.192(7.9); 1.122(3.3);
1.107(2.6); 0.146(1.3); 0.000(278.2); −0.150(1.4)
I-1-491:
HPLC-MS: logP = 2.57; mass (m/z): 387.1 (M + H)+; 1H-NMR(400.0 MHz, DMSO-D6): δ =
11.702(10.0); 8.486(9.8); 8.480(10.4); 8.376(9.7); 8.369(9.8); 8.285(2.7); 8.279(2.5); 8.264(2.9); 8.258
(5.1); 8.251(2.7); 8.237(2.7); 8.230(2.5); 7.778(0.8); 7.757(2.6); 7.748(1.5); 7.738(5.3); 7.722(8.2);
7.701(16.0); 7.684(4.6); 7.679(3.9); 6.981(12.1); 6.974(12.0); 3.518(1.0); 3.343(97.1); 3.002(0.4); 2.716
(0.5); 2.571(0.3); 2.563(0.7); 2.546(116.6); 2.530(0.6); 2.525(0.9); 2.516(12.3); 2.512(25.3); 2.507(34.0);
2.502(25.0); 2.498(12.2); 2.372(0.5); 0.000(1.4)
I-2-35
see synthesis Example C
I-2-66:
HPLC-MS: logP = 2.43; mass (m/z): 370.0 (M + H)+; 1H-NMR(400.0 MHz, DMSO-D6): δ =
11.900(6.8); 11.873(0.6); 8.770(0.9); 8.638(0.6); 8.632(0.7); 8.582(6.3); 8.576(6.6); 8.511(0.5); 8.462
(16.0); 8.436(0.3); 8.404(2.2); 8.397(2.1); 8.389(0.4); 8.383(2.3); 8.377(3.5); 8.372(2.1); 8.357(2.2);
8.351(2.0); 7.882(3.5); 7.862(4.4); 7.827(1.1); 7.808(3.1); 7.792(3.9); 7.772(5.7); 7.761(3.6); 7.757(4.0);
7.742(3.3); 7.724(1.2); 5.756(7.4); 3.324(31.3); 2.676(0.5); 2.672(0.6); 2.667(0.4); 2.525(2.1); 2.520(3.2);
2.512(34.8); 2.507(69.2); 2.503(90.5); 2.498(64.6); 2.494(30.5); 2.334(0.4); 2.330(0.6); 2.325(0.4);
1.989(1.2); 1.352(0.7); 1.337(3.0); 1.299(1.1); 1.259(1.6); 1.250(3.5); 1.234(1.0); 1.193(0.4); 1.175(0.7);
1.158(0.4); 0.008(2.2); 0.000(63.5); −0.009(2.1)
I-2-71:
HPLC-MS: logP = 2.51; mass (m/z): 388.0 (M + H)+; 1H-NMR(400.0 MHz, DMSO-D6): δ =
12.166(6.6); 8.587(6.2); 8.580(6.6); 8.475(16.0); 8.408(2.2); 8.402(2.0); 8.387(2.3); 8.382(3.5); 8.376(2.1);
8.362(2.2); 8.355(2.0); 7.832(0.5); 7.811(1.5); 7.802(0.9); 7.792(3.1); 7.777(5.0); 7.754(8.2); 7.737
(2.3); 7.731(2.7); 5.758(4.8); 3.330(26.6); 2.528(0.5); 2.515(11.2); 2.510(22.7); 2.506(29.8); 2.501
(21.1); 2.497(9.8); 1.991(0.7); 1.397(0.8); 1.177(0.4); 0.000(1.8)

1) Description of Method for Determination of the log P Values (Formic Acid Method)

The log P values given in the table were determined in accordance with EEC Directive 79/831 Annex V.A8 by HPLC (High Performance Liquid Chromatography) using a reversed-phase column (C 18). Temperature: 55° C.

Eluents for determination in the acidic range (pH 3.4):

Eluent A: acetonitrile+1 ml of formic acid/liter. Eluent B: water+0.9 ml of formic acid/liter.

Gradient: from 10% eluent A/90% eluent B to 95% eluent A/5% eluent B in 4.25 min.

Calibration was carried out using unbranched alkan-2-ones (having from 3 to 16 carbon atoms) with known log P values (the log P values were determined by the retention times using linear interpolation between two successive alkanones). The lambda max values were determined in the maxima of the chromatographic signals using the UV spectra from 200 nm to 400 nm.

2) Measurement of the NMR Spectra of Selected Examples

The NMR spectra were determined using a Bruker Avance 400 fitted with a flow probe head (volume 60 μl).

The NMR data for selected examples are listed either in conventional form (d values, number of hydrogen atoms, multiplet splitting) or as NMR peak lists.

The splitting of the signals was described as follows: s (singlet), d (doublet), t (triplet), q (quartet), quin (quintet), m (multiplet).

NMR peak list method

When the 1H NMR data for selected examples are noted in the form of 1H NMR peak lists, first the d value in ppm and then the signal intensity in round brackets are listed for each signal peak. The d value—signal intensity number pairs for different signal peaks are listed with separation from one another by semicolons.

The peak list for one example therefore takes the form of:

δ1 (intensity1); δ2 (intensity2); . . . ; δi (intensityi); . . . ; δn (intensityn)

The intensity of sharp signals correlates with the height of the signals in a printed example of an NMR spectrum in cm and shows the true ratios of the signal intensities. In the case of broad signals, several peaks or the middle of the signal and their relative intensities may be shown in comparison to the most intense signal in the spectrum.

For calibration of the chemical shift of the 1H NMR spectra we use tetramethylsilane and/or the chemical shift of the solvent, particularly in the case of spectra measured in DMSO. Therefore, the tetramethylsilane peak may but need not occur in the NMR peak lists.

The lists of the 1H NMR peaks are similar to the conventional 1H NMR printouts and thus usually contain all peaks listed in conventional NMR interpretations.

In addition, like conventional 1H NMR printouts, they may show solvent signals, signals of stereoisomers of the target compounds, which likewise form part of the subject-matter of the invention, and/or peaks of impurities.

In the reporting of compound signals in the delta range of solvents and/or water, our lists of 1H NMR peaks show the usual solvent peaks, for example peaks of DMSO in DMSO-d6 and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in Research Disclosure Database Number 564025.

The general concepts of the invention are described in the following biological examples, which are not to be considered as limiting.

Biological Example E

*Pratylenchus penetrans*—Test (Soil Application)
Solvent: 4 parts by weight acetone
Emulsifier: 1 part by weight alkylaryl polyglycol ether
To produce a suitable preparation of active compound, 1 part by weight of active compound is mixed with solvent and emulsifier at the ratio 4:1 and is diluted with water to the desired concentration.

This compound solution is mixed with 500 ml soil infected with *Pratylenchus penetrans* (800 nematodes per 100 ml). The stated concentration refers to the amount of compound per unit of volume soil (mg/l=ppm). The treated soil is filled into 500 ml pots and 3 corn seeds (*Zea mays*) are sown.

After 2 weeks the number of nematodes in the corn roots is determined by means of maceration. The roots are cleaned with water, cut into about 1 cm pieces and minced with water in a mixer for 10-15 seconds. The pieces are poured over a 0.2 mm-nematode sieve, rinsed with 400 ml water and the flow rate is collected. After 6 hours the supernatant is aspirated and the number of nematodes is determined microscopically with a counting chamber.

The average number of nematodes per pot is determined and efficieny is calculated by using Abbott's formula:

$$\text{Efficiency \%} = \left(1 - \frac{\text{number in } T \text{ after treatment}}{\text{number in } C}\right) \times 100$$

T=treated plants
C=untreated control plants
In this test, for example, the following compounds from the preparation examples showed good activity of 90% at an application rate of 2 ppm: I-2-35

In this test, for example, the following compounds from the preparation examples showed good activity of 88% at an application rate of 2 ppm: I-1-75

In this test, for example, the following compounds from the preparation examples showed good activity of 97% at an application rate of 4 ppm: I-1-574

Biological Example F

*Pratylenchus zeae*—Test (PRATZE Soil Application)
Solvent: 4 parts by weight acetone
Emulsifier: 1 part by weight alkylaryl polyglycol ether
To produce a suitable preparation of active compound, 1 part by weight of active compound is mixed with solvent and emulsifier at the ratio 4:1 and is diluted with water to the desired concentration.

This compound solution is mixed with 500 ml soil infected with *Pratylenchus zeae* (800 nematodes per 100 ml). The stated concentration refers to the amount of compound per unit of volume soil (mg/l=ppm). The treated soil is filled into 500 ml pots and 3 corn seeds (*Zea mays*) are sown.

After 2 weeks the number of nematodes in the corn roots is determined by means of maceration. The roots are cleaned with water, cut into about 1 cm pieces and minced with water in a mixer for 10-15 seconds. The pieces are poured over a 0.2 mm-nematode sieve, rinsed with 400 ml water and the flow rate is collected. After 6 hours the supernatant is aspirated and the number of nematodes is determined microscopically with a counting chamber.

The average number of nematodes per pot is determined and efficieny is calculated by using Abbott's formula:

$$\text{Efficiency \%} = \left(1 - \frac{\text{number in } T \text{ after treatment}}{\text{number in } C}\right) \times 100$$

T=treated plants
C=untreated control plants
In this test, for example, the following compounds from the preparation examples showed good activity of 89% at an application rate of 2 ppm: I-1-75

Biological Example G

*Radopholus similis*—Test (Soil Application)
Solvent: 4 parts by weight acetone
Emulsifier: 1 part by weight alkylaryl polyglycol ether
To produce a suitable preparation of active compound, 1 part by weight of active compound is mixed with solvent and emulsifier at the ratio 4:1 and is diluted with water to the desired concentration.

This compound solution is mixed with soil. The stated concentration refers to the amount of compound per unit of volume soil (mg/l=ppm). The treated soil is filled into 250 ml pots and a banana seedling is planted. Afterwards 2.5 ml of a nematode suspension (500 *Radopholus similis*/ml) are applied.

After 2 weeks the number of nematodes in the banana roots is determined by means of maceration. The roots are cut off, cleaned with water and after adding 25-40 ml 0.01% lactic acid—acid fuchsin solution they are boiled in a microwave. On the next day the roots are rinsed over a 0.025 mm-nematode sieve, roughly minced and macerated with 15-20 ml water in an Ultra Turrax. After filling up with water to 45 ml, the number of nematodes in the supernatant is determined microscopically with a counting chamber.

The average number of nematodes per pot is determined and efficieny is calculated by using Abbott's formula:

$$\text{Efficiency \%} = \left(1 - \frac{\text{number in } T \text{ after treatment}}{\text{number in } C}\right) \times 100$$

T=treated plants
C=untreated control plants

In this test, for example, the following compounds from the preparation examples showed good activity of 100% at an application rate of 2 ppm: I-1-140

In this test, for example, the following compounds from the preparation examples showed good activity of 90% at an application rate of 2 ppm: I-1-75

In this test, for example, the following compounds from the preparation examples showed good activity of 89% at an application rate of 2 ppm: I-1-491

In this test, for example, the following compounds from the preparation examples showed good activity of 88% at an application rate of 2 ppm: I-1-83

Biological Example H

*Globodera rostochiensis*—Test (Soil Application)
Solvent: 4 parts by weight acetone
Emulsifier: 1 part by weight alkylaryl polyglycol ether To produce a suitable preparation of active compound, 1 part by weight of active compound is mixed with solvent and emulsifier at the ratio 4:1 and is diluted with water to the desired concentration. This compound composition is mixed with soil. The stated concentration refers to the amount of compound per unit of volume soil (mg/l=ppm).

450 ml of this compound composition is mixed with 50 ml of soil infected with *Globodera rostochiensis* (20.000 nematodes/100 ml), filled in 500 ml pots and a potato seedling is planted.

After six weeks the average number of cysts in the potato roots per pot are determined and efficieny is calculated by using Abbott's formula:

$$\text{Efficiency \%} = \left(1 - \frac{\text{number in } T \text{ after treatment}}{\text{number in } C}\right) \times 100$$

T=treated plants
C=untreated control plants

In this test, for example, the following compounds from the preparation examples showed good activity of 100% at an application rate of 2 ppm: I-1-75, I-1-140, I-1-468, I-1-491, I-2-35, I-2-71

In this test, for example, the following compounds from the preparation examples showed good activity of 98% at an application rate of 2 ppm: I-2-66

In this test, for example, the following compounds from the preparation examples showed good activity of 80% at an application rate of 2 ppm: I-1-574

Biological Example I

*Meloidogyne incognita* in Tomato—Test (MELGIN Soil Application)
Solvent: 4 parts by weight acetone
Emulsifier: 1 part by weight alkylaryl polyglycol ether To produce a suitable preparation of active compound, 1 part by weight of active compound is mixed with solvent and emulsifier at the ratio 4:1 and is diluted with water to the desired concentration. The stated concentration refers to the amount of compound per unit of volume soil (mg/l=ppm).

This compound composition is mixed with 500 ml of soil and 4 ml of a nematode suspension (1000 differenciated eggs and larvae of *Meloidogyne incognita*/ml). The stated concentration refers to the amount of compound per unit of volume soil (mg/l=ppm). The treated soil is filled in 500 ml pots and a tomato seedling (*Solanum lycopersicum*) is planted.

After five weeks the average number of galls in the tomato roots per pot are determined and efficieny is calculated by using Abbott's formula:

$$\text{Efficiency \%} = \left(1 - \frac{\text{number in } T \text{ after treatment}}{\text{number in } C}\right) \times 100$$

T=treated plants
C=untreated control plants

In this test, for example, the following compounds from the preparation examples showed good activity of 100% at an application rate of 2 ppm: I-1-75, I-1-140, I-2-66, I-2-35

The invention claimed is:

1. A method of controlling nematodes comprising applying a compound of formula (I),

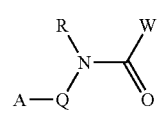

(I)

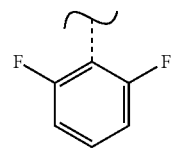

A-1

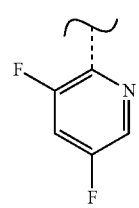

A-2

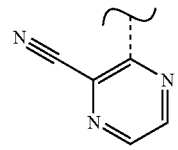

A-3

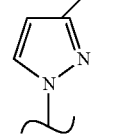

Q-1

-continued

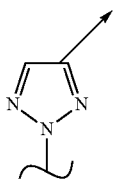

Q-2 wherein
A is A-1 or A-2 or A-3 in which the dotted line represents the bond to the N atom of Q,
Q is Q-1 or Q-2 in which the nitrogen is attached to ring A and the arrow in each case represents the bond to the NRCO moiety,
R is H or ethyl and
W represents a radical from the group consisting of W-1 to W-3

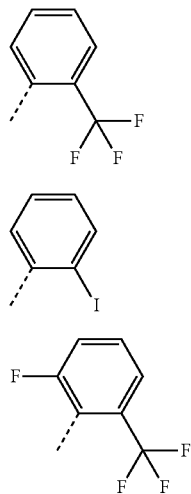

wherein the dotted line represents the bond to the C═O group,
to a plant, a part of a plant, or soil in which the plant grows, thereby to control the nematodes.

2. The method according to claim 1 wherein the plant is a vegetable crop.
3. The method according to claim 1 wherein the plant is a fruit crop.
4. The method according to claim 1 wherein the plant is a grape crop.
5. The method according to claim 1 wherein the plant is a pome fruit crop.
6. The method according to claim 1 wherein the plant is a stone fruit crop.
7. The method according to claim 1 wherein the plant is a nut crop.
8. The method according to claim 1 wherein the plant is a flower.
9. The method of claim 1, wherein the method increases yield of the plant.
10. The method according to claim 1, wherein the method kills nematodes.
11. The method according to claim 1, wherein the method curatively controls nematodes.
12. The method according to claim 1, wherein the method protectively controls nematodes.
13. The method according to claim 1, wherein the compound of formula (I) is applied as a plant drench application.
14. The method according to claim 1, wherein the compound of formula (I) is applied as a plant in-furrow application.
15. The method according to claim 1, wherein the compound of formula (I) is applied to a seed.
16. The method according to claim 1, wherein the compound of formula (I) is applied to soil in which the plant grows, wherein the soil is infested with nematodes.
17. The method according to claim 1, wherein the compound of formula (I) is applied to the plant or part of the plant.
18. The method according to claim 1, wherein
Q is Q-1,
A is A-1,
W is W-1, and
R is hydrogen.
19. The method according to claim 1, wherein
Q is Q-1,
A is A-1,
W is W-2, and
R is hydrogen.
20. The method according to claim 1, wherein
Q is Q-1,
A is A-2,
W is W-1, and
R is hydrogen.
21. The method according to claim 1, wherein
Q is Q-1,
A is A-2,
W is W-1, and
R is ethyl.
22. The method according to claim 1, wherein
Q is Q-1,
A is A-3,
W is W-1, and
R is hydrogen.
23. The method according to claim 1, wherein
Q is Q-2,
A is A-1,
W is W-1, and
R is hydrogen.
24. The method according to claim 1, wherein
Q is Q-2,
A is A-2,
W is W-1, and
R is hydrogen.
25. The method according to claim 1, wherein
Q is Q-2,
A is A-2,
W is W-3, and
R is hydrogen.

* * * * *